United States Patent
Bahou et al.

(10) Patent No.: US 10,543,286 B2
(45) Date of Patent: Jan. 28, 2020

(54) METHODS FOR INCREASING PLATELET COUNT BY INHIBITING BILIVERDIN IXβ REDUCTASE

(71) Applicant: The Research Foundation for The State University of New York, Albany, NY (US)

(72) Inventors: Wadie F. Bahou, Setauket, NY (US); Song Wu, Stony Brook, NY (US)

(73) Assignee: The Research Foundation for The State University of New York, Albany, NY (US)

(*) Notice: Subject to any disclaimer, the term of this patent is extended or adjusted under 35 U.S.C. 154(b) by 0 days.

(21) Appl. No.: 15/765,317

(22) PCT Filed: Oct. 5, 2016

(86) PCT No.: PCT/US2016/055446
§ 371 (c)(1),
(2) Date: Apr. 2, 2018

(87) PCT Pub. No.: WO2017/062422
PCT Pub. Date: Apr. 13, 2017

(65) Prior Publication Data
US 2018/0303958 A1   Oct. 25, 2018

Related U.S. Application Data

(60) Provisional application No. 62/238,236, filed on Oct. 7, 2015.

(51) Int. Cl.
C07H 21/04 (2006.01)
A61K 48/00 (2006.01)
A61P 7/02 (2006.01)
A61K 35/19 (2015.01)

(52) U.S. Cl.
CPC .......... *A61K 48/0066* (2013.01); *A61K 35/19* (2013.01); *A61K 48/0016* (2013.01); *A61K 48/0083* (2013.01); *A61P 7/02* (2018.01); *C12Y 103/01024* (2013.01)

(58) Field of Classification Search
CPC ...................................... A61K 48/00
See application file for complete search history.

(56) References Cited

U.S. PATENT DOCUMENTS

| | | | |
|---|---|---|---|
| 6,165,990 | A | 12/2000 | Singh et al. |
| 7,608,707 | B2 | 10/2009 | Khvorova et al. |
| 7,674,896 | B2 | 3/2010 | Khvorova et al. |
| 9,078,911 | B2 | 7/2015 | Lu |
| 2008/0069807 | A1 | 3/2008 | Jy et al. |

FOREIGN PATENT DOCUMENTS

| | | |
|---|---|---|
| EP | 2700949 A1 | 2/2014 |
| WO | WO 2008/014266 A9 | 1/2008 |

OTHER PUBLICATIONS

International Search Report dated Feb. 1, 2017 issued in PCT/US2016/055446.

*Primary Examiner* — Kimberly Chong
(74) *Attorney, Agent, or Firm* — Scully, Scott, Murphy & Presser, P.C.

(57) ABSTRACT

The present disclosure provides methods of treating a human having a disease or disorder that would benefit from increasing platelet counts. The method involves inhibiting the enzyme activity of biliverdin IXβ reductase (BLVRB) activity or inhibiting the expression of BLVRB gene.

13 Claims, 11 Drawing Sheets
(9 of 11 Drawing Sheet(s) Filed in Color)

j

METHODS FOR INCREASING PLATELET COUNT BY INHIBITING BILIVERDIN IXβ REDUCTASE

CROSS-REFERENCE TO RELATED APPLICATIONS

This application claims the benefit of U.S. Provisional Application No. 62/238,236 filed on Oct. 7, 2015, the entire contents of which are incorporated herein by reference.

STATEMENT REGARDING FEDERALLY SPONSORED RESEARCH

The present invention was made with government support under grant number HL119096 awarded by the National Institute of Health (NIH). The government has certain rights in the invention.

BACKGROUND OF THE DISCLOSURE

Platelets mediate the critical first-step in hemostasis (Bahou, W F, (2003) *Curr Top Dev Biol* 54, 343-369; Bahou, W F (2002) *Nat Med* 8, 1082-1083), and qualitative platelet disorders cause bleeding syndromes (Bahou, W F (2006) *Genomics and Clinical Medicine* (ed D. Kumar) 221-248 (Oxford University Press). Quantitative disorders of platelet number are associated with bleeding (thrombocytopenia; low platelet count), or thrombohemorrhage (thrombocythemia; high platelet count) (Vainchenker W et al., (2011) *Blood* 118(7):1723-1735; Kaser A, et al. (2001) *Blood* 98(9):2720-2725; Kaushansky K (2008) *Blood* 111(3):981-986; Bahou W F (2006) *Genomics and Clinical Medicine*, ed Kumar D (Oxford University Press, Oxford), pp 221-248; Bahou. W F (2012) *Thromb Res* 129 Suppl 1:S38-45; Debili N, et al. (1996) *Blood* 88(4):1284-1296; James C, et al. (2005) *Nature* 434(7037):1144-1148; Nangalia J, et al. (2013) *The New England journal of medicine* 369(25):2391-2405; Klampfl T, et al. (2013) *The New England journal of medicine* 369(25):2379-2390)

About $1\times10^{11}$ platelets are produced daily by megakaryocyte (MK) formation, which is largely controlled by the TPO/c-MPL (thrombopoietin/c-myeloproliferative ligand receptor) axis, and derived from common bi-potent megakaryocyte-erythrocyte progenitors (MEP) (Debili, N. et al. (1996) *Blood* 88, 1284-1296). Human blood platelets stop bleeding, and low platelet counts cause life-threatening hemorrhage. Approaches to temporarily correct low platelet counts include platelet transfusions from donors which are difficult to obtain and are costly, and medications. However, medications are known to be associated with adverse effects such as platelet activation, blood clotting, worsening of platelet counts, and bone marrow scarring.

To date, approaches for enhancing platelet production have focused on the TPO/c-MPL axis. Three general classes of second-generation TPOs are currently in development: (i) TPO peptide mimetics, (ii) TPO nonpeptide mimetics, and (iii) TPO antibody mimetics. While these drugs show efficacy in enhancing platelet production, their direct receptor binding/activation mechanism(s) have raised concerns relative to platelet activation, secondary thromboembolic complications, rebound thrombocytopenia, and increased bone marrow reticulin formation (Liebman, H A and Pullarkat, V (2011) *Hematology Am Soc Hematol Educ Program* 2011, 384-390).

SUMMARY OF THE DISCLOSURE

The present disclosure provides methods and compositions for treating a human having a disease or disorder that would benefit from increasing platelet counts. These methods and compositions target a pathway distinct which is distinct from the pathways targeted thus far, and are based on the recognition that the oxidation-reduction (redox) activity of the heme degradation pathway enzyme biliverdin 1×β reductase (BLVRB) functions in a regulatory pathway that governs megakaryocyte lineage determination, and that reduced enzymatic activity of the enzyme favors increased platelet production.

Accordingly, in one aspect, the present disclosure provides a method of treating a human having a disease or disorder that would benefit from increasing platelet counts. The method includes administering to the subject a therapeutically effective amount of an agent that inhibits biliverdin IXβ reductase (BLVRB) enzymatic activity, thereby treating the subject.

In one embodiment, the agent is a chemical compound.

In one embodiment, the BLVRB enzymatic activity is inhibited by at least about 30% to about 100%.

According to another aspect, the present disclosure provides a method of treating a human having a disease or disorder that would benefit from increasing platelet counts. The method includes administering to the subject a therapeutically effective amount of an agent that inhibits the expression of biliverdin IXβ reductase (BLVRB) gene, thereby treating the subject.

In one embodiment, the agent is a small interfering RNA (siRNA) molecule or an anti sense oligonucleotide specific to a region in the mRNA of BLVRB gene.

In one embodiment, the BLVRB gene expression is inhibited by at least about 30% to about 100%.

According to yet another aspect, the present disclosure provides a pharmaceutical composition comprising a chemical compound that inhibits the enzymatic activity of BLVRB.

In one embodiment, the BLVRB enzymatic activity is inhibited by at least about 30% to about 100%.

According to yet another aspect, the present disclosure provides a pharmaceutical composition that inhibits the expression of BLVRB gene, the composition including a small interfering RNA (siRNA) molecule or an antisense oligonucleotide specific to a region in the mRNA of the gene for BLVRB gene.

In one embodiment, the BLVRB gene expression is inhibited by at least about 30% to about 100%.

In one embodiment, the agent is administered at a dose of about 0.01 mg/kg to about 50 mg/kg.

In one embodiment, the inhibition of BLVRB enzymatic activity or BLVRB gene expression leads to increased thrombopoiesis.

In one embodiment, the inhibition of BLVRB enzymatic activity or BLVRB gene expression leads to accumulation of reactive oxygen species (ROS).

In one embodiment, the disease or disorders one selected from the group comprising: decreased production of platelets, increased breakdown of platelets, increased use of platelets, and trapping of platelets in the spleen. The decreased production of platelets is caused, for example, by one of: cancer, anemia, viral infection, chemotherapy, or heavy alcohol consumption. For example, the cancer is leukemia, lymphoma, or any cancer involving solid organs such as lung, gastrointestinal, genitourinary, gynecological, musculoskeletal, or cancers involving the head and neck. For example, the increased breakdown of platelets is caused by one of: pregnancy, autoimmune disease, and medications.

For example, the increased use of platelets occurs due to the disorder thrombotic thrombocytopenic purpura.

BRIEF DESCRIPTION OF THE DRAWINGS

The patent or application file contains at least one drawing executed in color. Copies of this patent or patent application publication with color drawing(s) will be provided b the Office upon request and payment of the necessary fee.

The present disclosure will be better understood by reference e following drawings of which:

FIG. 3c shows specific activity for reducing Flavin (flavin reductase activity, FR) using 100 μM flavin mononucleotide, and FIG. 2D shows specific activity for reducing biliverdin (beliverdin reductase activity, BVR) using 20 μM BV dimethyl esters (Franklin E M, et al. (2009) The FEBS journal 276(16):4405-4413). (N=6, expressed as mean±SEM); ****p<0.00001.

DETAILED DESCRIPTION

Figure 1:
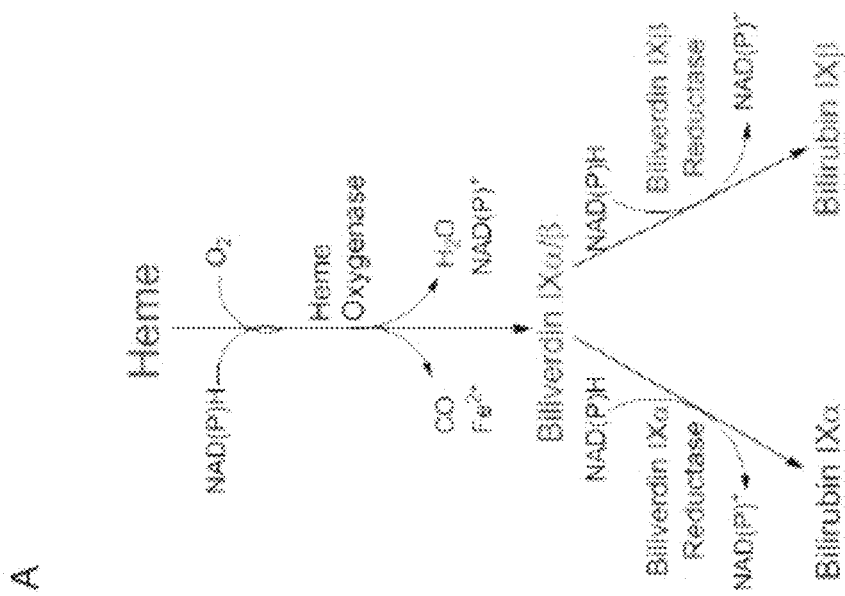
FIG. 1 is a schematic diagram of heme degradation pathway and shows biliverdin IXβ catalyzed reduction of biliverdin IXβ to bilirubin IXβ

The methods disclosed herein are predicated in part on the finding that the oxidation-reduction (redox) activity of the twine degradation pathway biliverdin (BV) IXβ reductase (BLVRB) plays an important role in a regulatory pathway governing megakarypcyte lineage fate in humans. As shown in the schematic diagram of heme degradation in FIG. 1, BLVRB is an NAD(P)H-dependent flavin reductase that functions during terminal heme degradation, downstream of heme oxygenase. Specifically, BLVRB catalyzes the reduction of biliverdin IXβ to bilirubin IXβ.

The disclosure describes platelet transcriptome sequencing and extended thrombocytosis cohort analyses which were carried out and which led to the identification of a single loss-of-function mutation (BLVRB$^{S111L}$) in the enzyme that was causally associated with both clonal (Vainchenker W et al., (2011) Blood 118(7):1723-1735) and non-clonal (Kaser A, et al. (2001) Blood 98(9):2720-2725) disorders of enhanced platelet production. BLVRB$^{S111L}$ is a member of the family of nucleotide (substrate/cofactor) binding proteins having an α/β dinucleotide NAD(P)H binding fold, and furthermore, it is functionally defective with respect to redox coupling measured using both flavin and verdin (BV IXβ) dimethyl esters tetrapyrolle(s). This defect in redox-coupling leads to differential reactive oxygen species (ROS) accumulation in a multipotential progenitor cell during a developmentally-restricted window of fate determination, which promotes commitment to the megakaryocyte lineage. The data described herein define the first physiologically-relevant function of BLVRB, and implicate its activity and heme-regulated BV tetrapyrrole(s) in a unique redox-regulated pathway governing terminal megakaryocytopoiesis. These observations define BLVRB as a protein that can be targeted with redox-inhibiting BLVRB agents, distinct from current TPO mimetics currently under development, for increasing platelet counts. Described immediately below is the identification and functional characterization of the S111L mutation in BLVRB.

Megakaryocytopoiesis and proplatelet formation represent progressively linked stages of hematopoietic stem cell development that maintain the normal circulating pool of platelets (Kaushansky K (2008) Blood 111(3):981-986). Platelets are critical to normal hemostasis, pathological thrombosis, and host adaptive immunological responses (Bahou W F (2006) Genomics and Clinical Medicine, ed Kumar D (Oxford University Press, Oxford), pp 221-248; Bahou W F (2012) Thromb Res 129 Suppl 1:S38-45). Platelet generation ($\sim 1 \times 10^{11}$ cells daily) is largely controlled by the thrombopoietin (TPO) gene/c-Mpl (TPO receptor) axis or the (TPO)/c-MPL axis, and is a result of the commitment of the common bipotent megakaryocyte-erythrocyte progenitors (MEP) to the megakaryocyte (MK) lineage (Debili N, et al. (1996) Blood 88(4):1284-1296). Although MKs are reduced in MPL-deficient mice, animals still produce MKs and platelets, implying that hematopoietic stem cells (HSCs) maintain the capacity for lineage fate in the absence of MPL. Transcription factors including GATA-1, GATA-2, FOG1/ZFPM1, RUNX1, and NFE2, are important for MK development (Bahou W F (2006) Genomics and clinical Medicine, ed Kumar D (Oxford University Press, Oxford), pp 221-248), but none exclusively specify MK fate (Kaushansky K (2008) Blood 111(3):981-986). While human blood counts have a heritable component, known genetic loci account for 5% of platelet variability (Gieger C, et al. (2011) Nature 480(7376):201-208), highlighting the considerable knowledge gap of genetic pathways regulating physiological and pathological thrombopoiesis.

The human gene mutations described herein and which modulate blood-cell production were revealed by applying large-scale platelet transcriptome sequencing to cohorts with myeloproliferative neoplasms (MPN), which are hematopoietic disorders characterized by overproduction of various terminally differentiated blood cells, either because of hypersensitivity or independence from cytokine regulation (Vainchenker W et al., (2011) Blood 118(7):1723-1735) (4) (FIG. 1a), MPN subtypes display genetic commonalties leading to increased JAK-STAT signaling, linked by function mutations involving Janus kinase 2 ($JAK2^{V617F}$) (James C, et al. (2005) Nature 434(7037):1144-1148), or CALR in non-imitated JAK (Nangalia J, et al. (2013) The New England journal of medicine 369(25):2391-2405; Klampfl T, et al. (2013) The New England journal of medicine 369(25):2379-2390). Their broad phenotypic heterogeneity suggested that rare allelic variants (genomic modifier loci) affecting blood cell counts could be phenotypically unmasked in clonally-expanded hematopoietic disorders.

Figure 5:
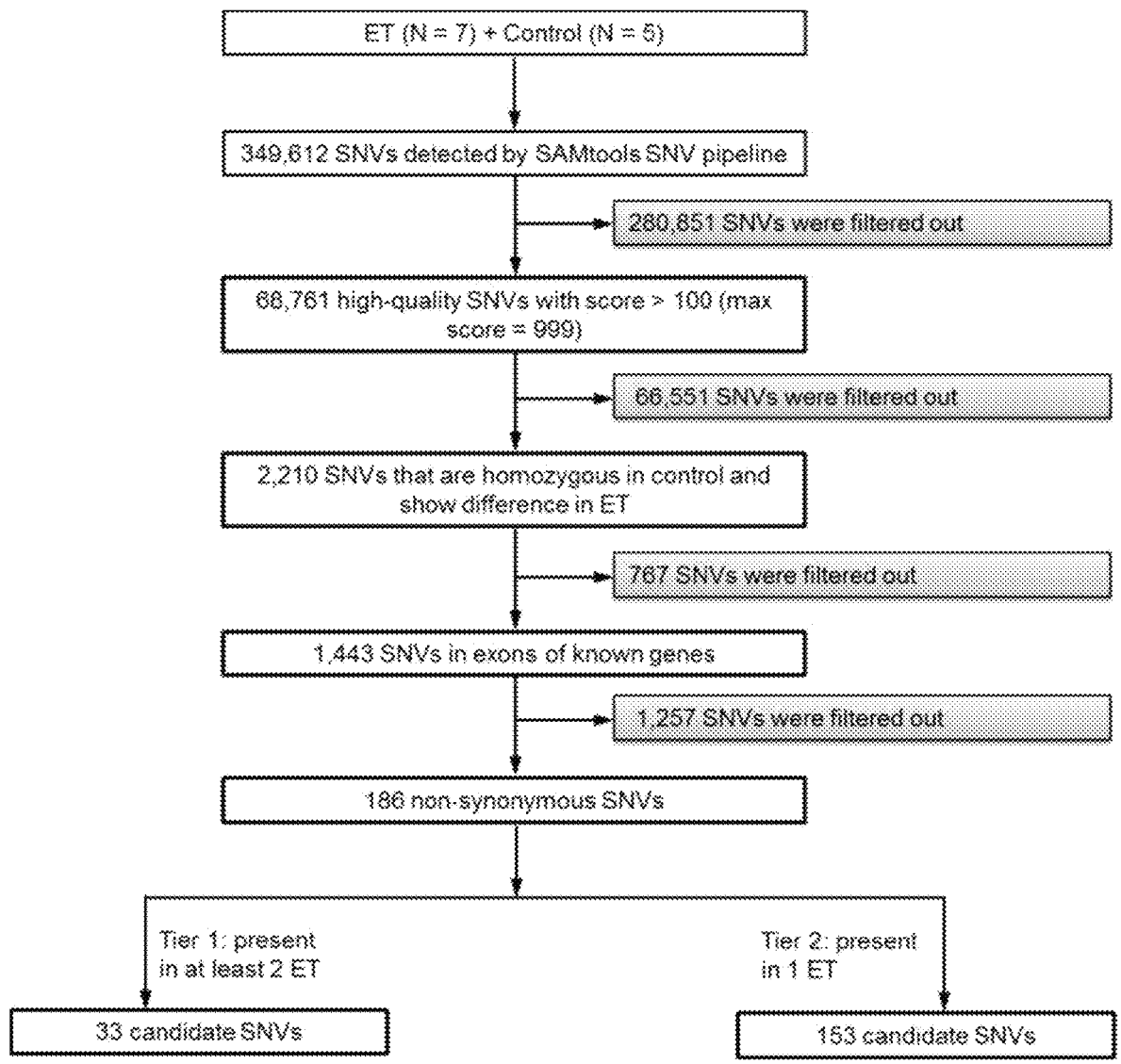
FIG. 5 is a flow chart for the algorithm for detecting SNV.

To identify these genetic modifier loci, RNA sequencing (RNA-Seq) was performed from highly-purified platelets from seven MPN subjects subclassified with essential thrombocythemia (ET) (Gnatenko D V, et al. (2010) Blood 115(1):7-14). Four harbored the $JAK2^{V617F}$ mutation and three were genotypically normal (GIG)]. In addition there were five healthy controls. An iterative algorithm was developed to identify non-synonymous single nucleotide variants (nsSNVs) as causally-plausible candidate genes. Of the ~350,000 SNVs, 186 high-quality nsSNVs were identified, of which 33 qualified as Tier 1 based on a stringent filtering step designed to exclude private mutations (FIG. 5). It was found that 86% of evaluable gene/SNPs had minor allelic frequencies <2%, validating the strategy for identifying rare novel modifier genes using relatively small sample subsets from a clonally-expanded hematopoietic disorder.

The candidate nsSNV list included $JAK2^{V617F}$, although neither the initial screen nor targeted visualization of previously-described MPN defects (Vainchenker W et al., (2011) Blood 118(7):1723-1735) including MPL or CALR (Nangalia J, et al. (2013) The New England journal of medicine 369(25):2391-2405; Klampfl T, et al. (2013) The New England journal of medicine 369(25):2379-2390) were identified. Other than JAK2, none of the gene/SNVs identified have previously been described as MPN modifiers, or overlapped with genetic loci modulating megakaryocyte (MK)/platelet (Gieger C, et al. (2011) Nature 480(7376): 201-208) or erythroid (van der Harst P, et al. (2012) Nature 492(7429):369-375) parameters in humans.

Figure 2:
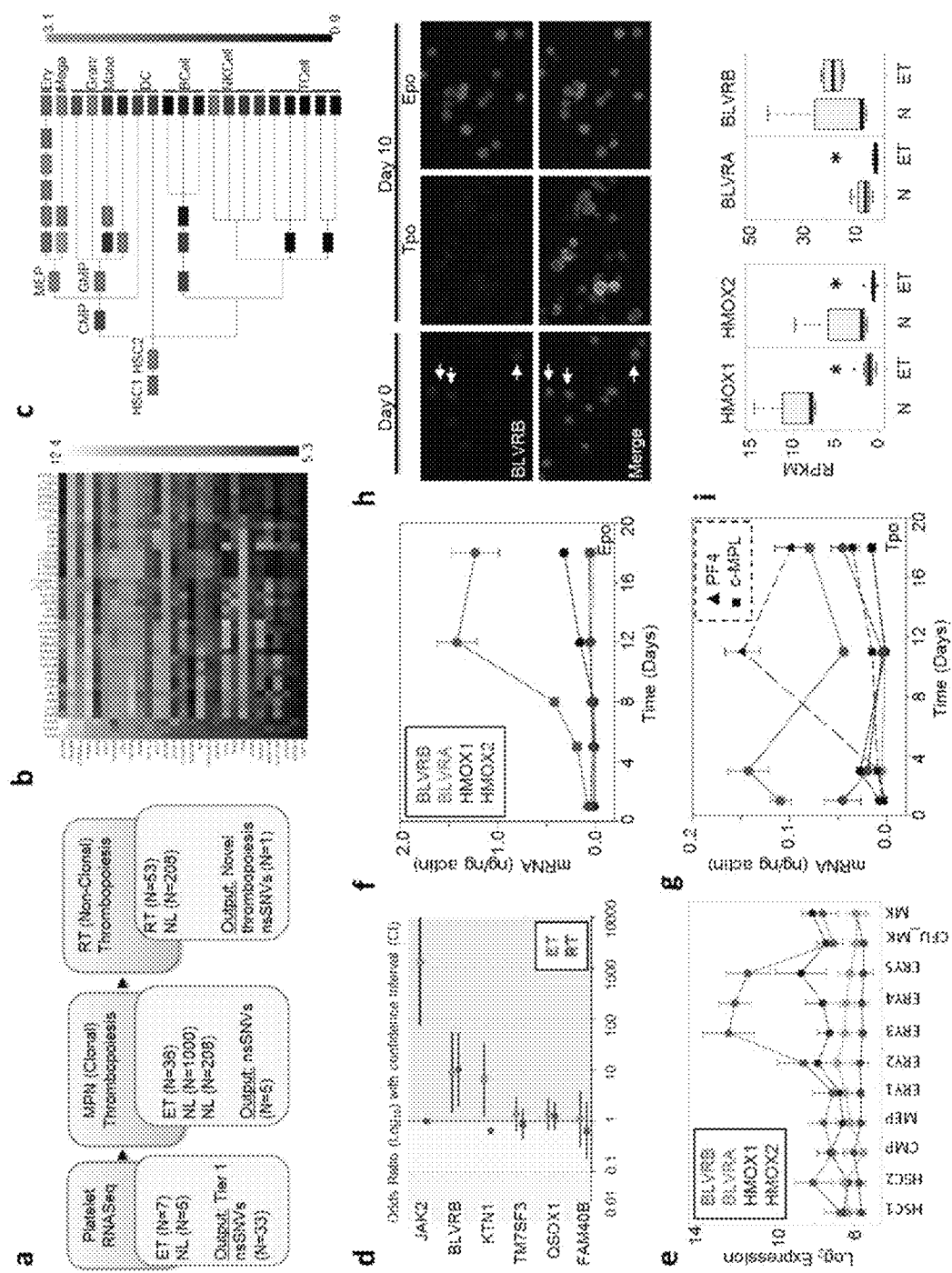
FIG. 2a is work-flow schematic diagram detailing phenotypic cohorts that were genetically studied (sample numbers in parenthesis) and output SNVs (single nucleotide variants) at critical validation and genetic association steps.
FIG. 2b is a heat map generated using expression profiles (Novershtern N, et al. (2011) Cell 144(2):296-309) for the candidate gene subset (N=29) encompassing oligonucleotide probes on the Affymetrix HG_U133AAofAv2 array (scale bar on right).
FIG. 2c is a schematic diagram of hematopoietic lineage displayed as a Wilcoxon signed-rank test of the t-statistic ($-\log_{10}$ P) calculating the likelihood that the 29 member gene subset is more greatly expressed relative to all other genes expressed in at least one time point by lineage (scale bar on right).
FIG. 2d is a graph showing Odds Ratios (OR) with confidence intervals calculated by thrombocytosis phenotype using genotype-matched validation controls (N=208); only BLVRB$^{S111L}$ was observed to remain a strong risk allele irrespective of thrombocytosis etiology (RT OR=10.2, CI 1.96-53.6; p=0.005).
FIG. 2e is a graph showing E/Meg-restricted expression of the heme degradation pathway genes using in silico data (Novershtern N, et al. (2011) Cell 144(2):296-309). A $\log_2$ signal intensity <6 is considered background expression.
FIGS. 2f and 2g are graphs showing expression patterns of heme degradation pathway genes quantified by Q-PCR using human CD34$^+$ cells differentiated along erythroid (Epo) (FIG. 10 or megakaryocytic (Tpo) (FIG. 2g) lineages. Tpo-directed cultures include Platelet Factor 4 (PF4) and c-MPL transcripts as lineage markers. All results are expressed as actin-normalized means±SEM from triplicate wells.
FIG. 2h is a set of immunofluorescent micrographs of expression of BLVRB and CD41a obtained using CD34$^+$ HSCs and differentiated along megakaryocyte (Tpo) or erythroid (Epo) lineages. The micrographs demonstrate early (D0) BLVRB expression (preceding CD41a), with low-level expression in terminally-differentiated MK cultures and reciprocal up-regulation in erythroid-differentiated cultures (Day 10). Merged images correspond to composite overlays of phycoerythrin-conjugated anti-BLVRB (upper panel), FITC-conjugated anti-CD41a (lower panel), and nuclear 4',6-diamidino-2-phenylindole (lower panel); magnification 400×(all images were captured using identical exposure times).
FIG. 2i is a graph showing RNA levels (normalized RPKM [reads per kb per 1×10$^6$ cells) of heme degradation pathway genes from ET (N=7) and normal (N=5) platelets; *p-values<0.05.

Gene expression patterns of the candidate genes were analyzed using an atlas of 38 distinct hematopoietic cell types (Novershtern N, et al. (2011) Cell 144(2):296-309). Of these, 29 genes were represented on the Affymetrix gene array (FIG. 2b), and candidate transcripts were enriched on average in early-stage MEP and granulocyte/monocyte progenitor (GMP) cells compared to non-candidate transcripts in the same cell lineage (FIG. 2c). These aggregate lineage expression patterns became more restricted in terminally-differentiating megakaryocytes and erythroblasts (both early and late stages), with less exaggerated (but present) lineage-enrichment in myeloid subsets (colony forming unit-granulocyte [CFU-G] and early-stage neutrophilic metamyelocytes). Limited expression was observed in lymphoid cells (B-cells, T-cells and Natural Killer (NK) cells), collectively highlighting that the candidate genes are enriched in all three hematopoietic lineages encompassing the clonal evolution of MPNs, and under-represented (or excluded) in lymphoid cells whose genetic composition is generally considered germ line in origin.

Figure 6:
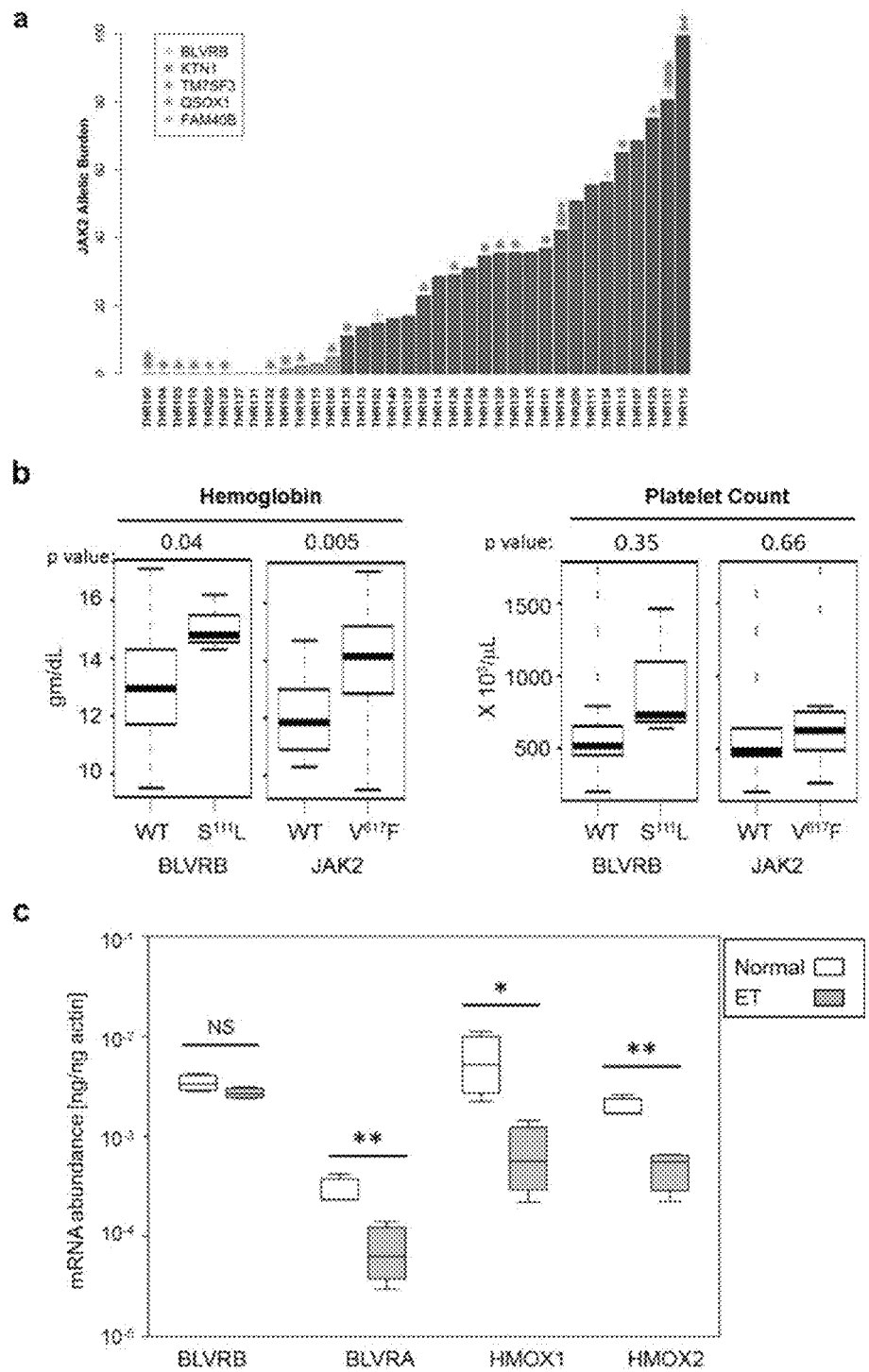
FIG. 6a is a graph showing the genotype distribution across the ET cohort 36) by JAK2$^{V617F}$ allelic burden as quantified by pyrosequencing.
FIG. 6b is a set of two graphs showing hemoglobin counts (left) and platelet counts (right) plotted according to genotype (wild-type vs. mutant). Individual box plots show median encompassed within first and third quartiles, with 95% confidence intervals.
FIG. 6c is a graph showing results of Platelet Q-PCR performed using mRNA from ET (N=4) or healthy controls (N=5), depicted as box plots. p*<0.05; **<0.01.

Genotypic studies of the 33-member SNVs was carried out using an expanded ET cohort (N=36) (Gnatenko D V, et al. (2010) Blood 115(1):7-14). Statistical association analyses were performed using (i) genotypic frequencies of healthy controls from the 1000 Human Genomes Project (Anonymous (2012) Nature 491(7422):56-65) (15)) and (ii) an independently-genotyped secondary cohort of healthy controls (N=208), and it was established that five SNVs (excluding $JAK2^{V617F}$) were associated with the ET phenotype. The five nsSNVs were distributed almost evenly across all samples suggesting that their mutation status is independent of JAK2 allelic burden (FIG. 6A). Mutations involving BLVRB (gene description: Biliverdin Reductase B (Flavin Reductase (NADPH)); chromosome 19q13.1-q13.2; position40964064; SNV/SNP rs149698066 (www.ncb.nlm.nih.gov/SNP); allele GA; mutation S111L; OR (odds ratio) 31.67; p=0.006) and KTN1 (OR 17.32; p=0.0018) represented the strongest thrombocytosis risk alleles. The TM7SF3 SNV was a moderate risk allele (OR 2.93; p=0.005), while SNVs involving QSOX1 (OR 1.96;

p=0.06), and FAM40B/STRP2 (OR 3.02; p=0.09) only approached statistical significance. The independent (i.e. driver) nature of these SNVs was established by genotyping a new subject cohort with reactive thrombocytosis (RT, N=53), a non-clonal disorder of exaggerated platelet production due to interleukin-6 (IL-6)-induced thrombopoietin (TPO) release (Kaser A. et al. (2001) *Blood* 98(9):2720-2725). This approach restricted the gene/SNVs to the subset functioning as modifiers of platelet production independent of JAK2$^{V617F}$ and/or dominant subclones harboring additional molecular abnormalities (Vainchenker W, (2011) *Blood* 118(7):1723-1735. Only BLVRB$^{S111L}$ retained its significance as a thrombocytosis risk allele (FIG. 2d). Substratification analysis established that JAK2$^{V617F}$ and BLVRB$^{S111L}$ were uniquely associated with exaggerated hemoglobin levels in the MPN background (FIG. 6b).

The BLVRB gene product biliverdin IXβ reductase and its structurally-distant homologue BLVRA (biliverdin IXα reductase) function downstream of heme oxygenase(s)-1 (inducible HMOX1) and -2 (constitutive HMOX2) within the heme degradation pathway to catalyze reduction of biliverdin (BV) IXα (or IXβ) tetrapyrrole(s) to the potent antioxidants bilirubin (BR) IXα and IXβ (FIG. 1) (Sedlak T W, et al. (2009) *Proceedings of the National Academy of Sciences of the United States of America* 106(13):5171-5176; Baranano D E, et al., (2002) *Proceedings of the National Academy of Sciences of the United States of America* 99(25):16093-16098), characterized as a methemoglobin reductase (Xu F, et al., (1992) *Proceedings of the National Academy of Sciences of the United States of America* 89(6):2130-2134.), retaining physiological relevance primarily as an oxidation-reduction (redox) coupler in the presence of methylene blue for treatment of acquired or congenital methemoglobinemia (CYB5A deficiency, OMIM #250800), BLVRB's function(s) remain additionally enigmatic because it catalyzes formation of the only robin generated during fetal hematopoiesis (the IXβ isomer) (Pereira P J, et al. (2001) *Nat Struct Biol* 8(3):215-220). Expression patterns of the four heme degradation pathway genes along E/Meg lineage development was analyzed using data extracted from platelet (Gnatenko D V, et al. (2003) *Blood* 101(6):2285-2293) and genetic atlases (Novershtern N, et al. (2011) *Cell* 144(2):296-309). The patterns demonstrated a striking approximately 40-fold induction of BLVRB, which was most pronounced during the terminal phases of erythroid formation (FIG. 2e). This induction was in sharp contrast to BLVRA expression, which remained generally stable (or diminished) throughout the same differentiation period. In silica expression patterns were recapitulated in Epo (erythropoietin)-induced CD34$^+$ cultures, but were temporally distinct from those obtained using Tpo (MK)-directed cultures where BLVRB induction peaked at an early (Day 3/4) time point. Although absolute MK BLVRB peak transcript abundance remained considerably less 10%) than that in late-stage erythroid progenitors, peak levels were comparable to (but preceding) those of the MK commitment marker platelet factor 4 (PF4) (Gnatenko D V, et al. (2003) *Blood* 101(6):2285-2293), and remained higher than those of MPL (FIG. 2f-g). These lineage- and temporally-dichotomous BLVRB expression patterns were recapitulated by immunofluorescence stains. BLVRB expression remained primarily cytoplasmic with some suggestions for nuclear co-localization in late-stage erythroid cultures (FIG. 2h). Finally, extraction of the RPKM scores from the RNASeq data (FIG. 2i) and confirmatory Q-PCR measurements (FIG. 6c) demonstrated statistically-significant down-regulation of BLVRA, HMOX1, and HMOX2 in ET platelets. Only the BLVRB mRNA remained unchanged. These expression patterns collectively suggested a BLVRB function distinct from that of other heme degradation pathway genes during E/Meg lineage commitment.

Figure 3:
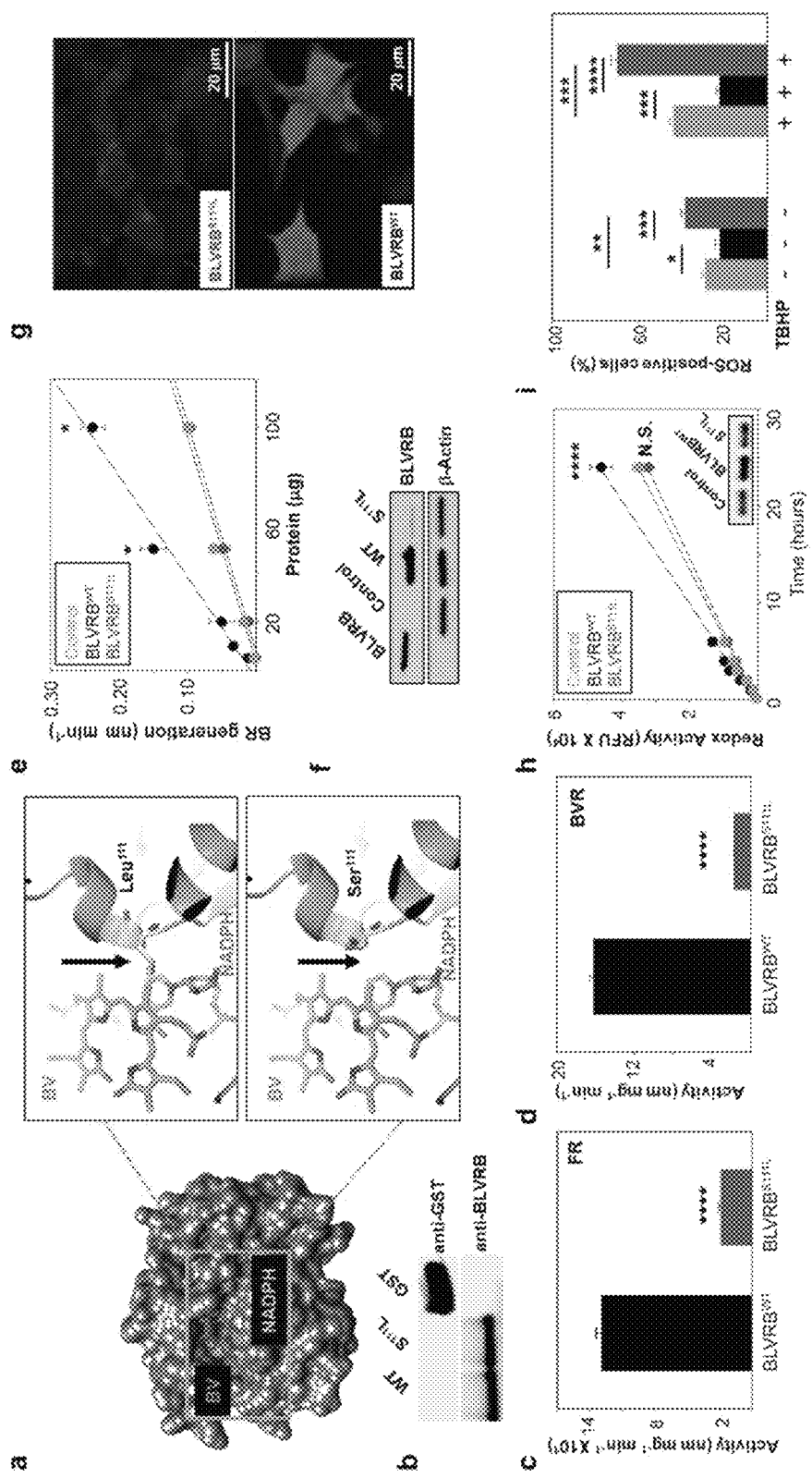
FIG. 3a is a globular protein structure displaying BLVRB$^{S111L}$ mutation (light sphere s to the left of "BV") within the single biliverdin (BV)/NAD(P)H binding fold. Insets show higher resolution ribbon s modeled to predict interactions of mutant Leu$^{111}$ or native Ser$^{111}$ with BV and NADPH. It may be noted that Ser$^{111}$ is uniquely positioned for recognition and/or proton transfer within the Rossmann binding fold. Predicted proximity interference by the hydrophobic Leu$^{111}$ aliphatic isobutyl side chain is also shown (arrow). Models were generated using PYMOL software (Pereira P J, et al. (2001) Nat Struct Biol 8(3):215-220), based on NADP/mesobiliverdin IVα ternary (PDB ID#1HE3) and NADP/FMN ternary (PDB ID#1HE4) complexes.
FIG. 3b is an immunoblot of purified recombinant BLVRB enzymes after cleavage by thrombin and glutathione affinity chromatography to deplete GST (50 ng/lane).
FIGS. 3c and 3d are graphs showing activities of recombinant BLVRB$^{WT}$ and BLVRB$^{S111L}$.
FIG. 3e shows BVR activity determination using solubilized lysates from Lv-infected HEK293 cells in the presence of 20 μM BV dimethyl esters (N=3); *p<0.05. The upper line corresponds to the activity of the wild type enzyme. Among the two lower lines, the upper one (with light filled circles) corresponds to the activity of a control vector (empty virus) and the lower one (with dark filled circles) to that of BLVRB$^{S111L}$.
FIG. 3f is an immunoblot of lysates from Lv-infected HEK293 cells (20 μg/lane) for measuring levels of BLVRB enzymes. Lane 1 is a positive control loaded with 50 ng pure enzyme.
FIG. 3g is a set of immunofluorescent micrographs of Lv-infected HEK293 cells demonstrating attenuated but identical (primarily cytoplasmic) expression pattern of BLVRB$^{S111L}$ compared to that of BLVRB$^{WT}$. Mean integrated fluorescence intensity (IFI) of BLVRB$^{S111L}$ is 281±18, and that of BLVRB is 849±47.
FIG. 3h is a graph showing redox activity of genetically-modified CD34$^+$ NCRM1 iPSCs. For determining the redox activity, about 1×10$^4$ cells/well were loaded with 0.1 v/v resazurin, and time-dependent spectrofluorimetric detection (530 nm excitation, 590 nm emission) of reduced resorufin was carried out. The data are expressed as mean±SEM of relative fluorescent units (RFU, N=6). Inset shows cellular BLVRB expression, 20 μg lysates/lane. ****p<0.0001. The upper straight line corresponds to redox activity from cells transduced with BLVRB$^{WT}$. Among the two lower lines, the upper one (with light filled circles) corresponds to the redox activity from cells transduced with a control vector (empty virus) and the lower one (with dark filled circles) to that from cells transduced with BLVRB$^{S111L}$.
FIG. 3i is a bar graph showing ROS expression by genetically-modified NCRM1 iPSCs. About 1×10$^5$, cells were labeled as in FIG. 2h, and treated (or not) with 200 μM tert-butyl hydroperoxide (TBHP) for 1 hour at 37° C., and ROS-expressing cells were quantitated by flow cytometry after a 60 minute period loading with cell-permeable Cell-ROX Green (500 nM) as indicator (N=6); p-values *<0.05; <0.01; *<0.001; ****<0.0001. From left to right, the bars correspond to activity in control cells, activity in cells having BLVRB$^{WT}$, and activity in cells having BLVRB$^{S111L}$.
FIG. 3j is a set of two graphs comparing BLVRB flavin reductase (upper panel) and biliverdin reductase activity (lower panel) for each of BLVRB$^{WT}$ and BLVRB$^{S111L}$.
Figure 3:
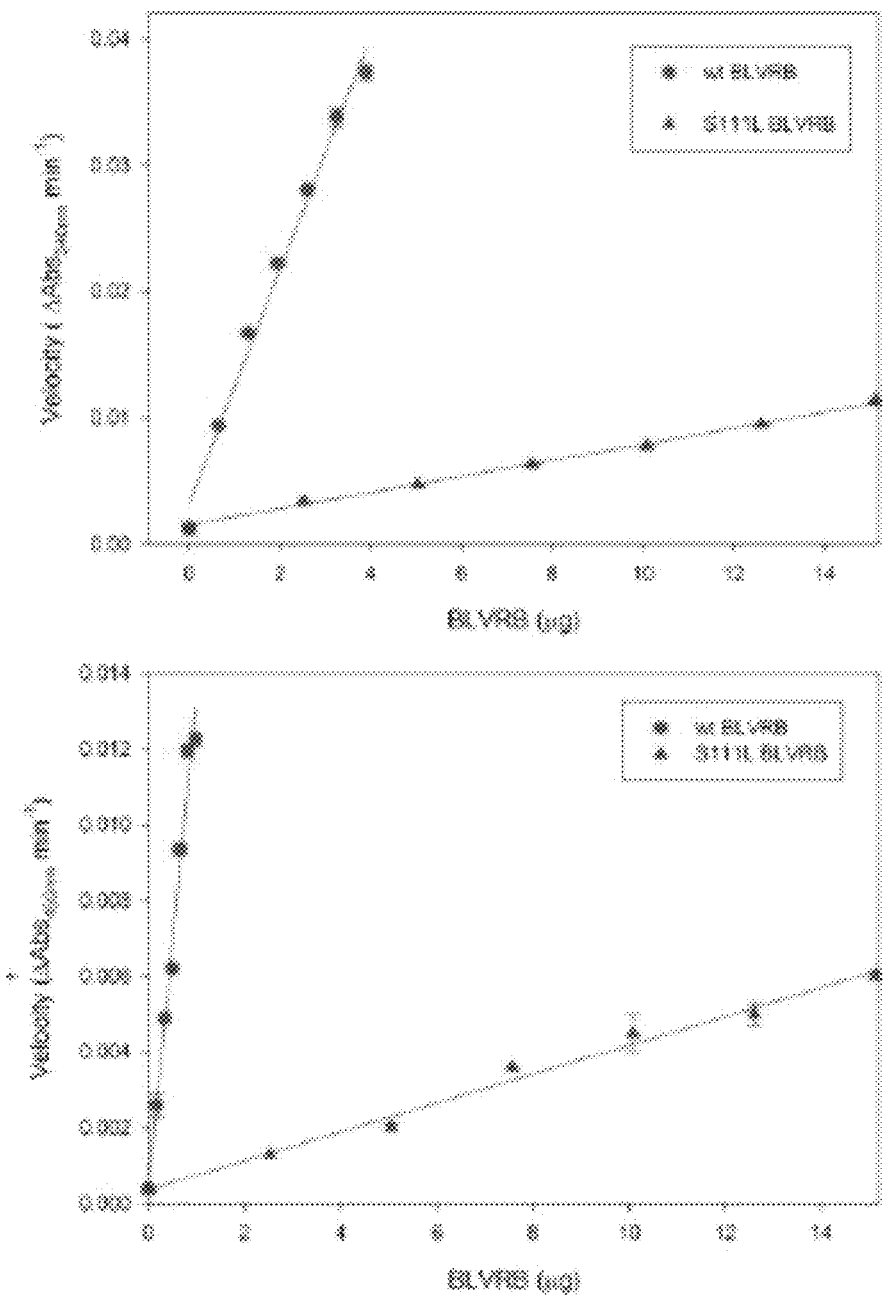
Figure 7:
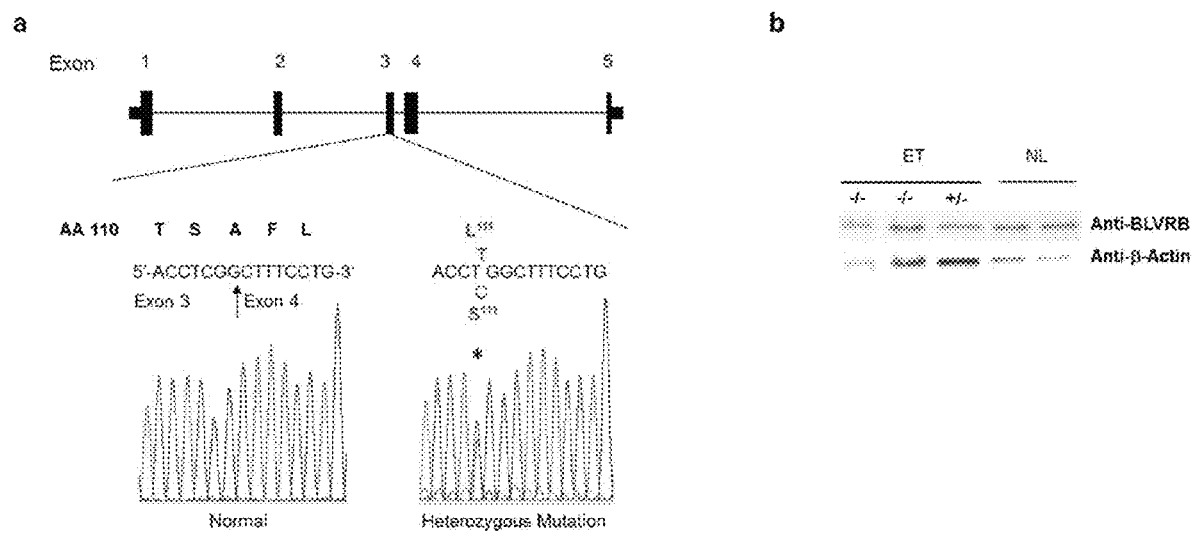
FIG. 7a is a schematic diagram showing the Exon/intron structure of the BBLVRB gene with the S111L mutation, and a sequencing profile showing the mutation (asterisk).
FIG. 7b is an immunoblot performed using 20 μg solubilized platelet lysates from healthy controls (NL) or ET patients without (−/−) or heterozygous (+/−) for the BLVRB$^{S111L}$ mutation.

Comprehensive BLVRB sequence analysis in the complete ET cohort identified no additional mutations or alterations of platelet BLVRB protein expression, prompting more focused analysis of the BLVRB 462$^{C \rightarrow T}$ (S$^{111}$L) heterozygous mutation (FIGS. 7a and 7b). Previously-characterized crystal structure of the 206 aa biliverdin IXβ reductase revealed a monomeric protein with a dinucleotide Rossmann binding fold that preferentially accommodates NAD(P)H as electron donor with promiscuous binding of various linear tetrapyrroles as electron acceptors (Xu F, Quandt K S, & Hultquist D E (1992) *Proceedings of the National Academy of Sciences of the United States of America* 89(6):2130-2134; Pereira P J, et al. (2001) *Nat Struct Biol* 8(3):215-220) (FIG. 3a). Ser$^{111}$ embedded within the wide D$^{80}$-K$^{120}$ substrate binding pocket is structurally homologous to catalytic serines within UDP-galactose epimerase (Ser$^{124}$) (Thoden J B et al., (1996) *Biochemistry* 35(8):2557-2566) and ferredoxin-NADP$^+$ reductase (Ser$^{49}$) (Niviere V et al., (1996) *The Journal of biological chemistry* 271(28):16656-16661), and uniquely positioned for recognition and/or proton transfer between flavin isoalloxazine and nicotinamide rings (Franklin E M, et al. (2009) *The FEBS journal* 276(16):4405-4413). It is believed that the S$^{111}$L mutation leads to an interference with the recognition and/or hydride transfer between flavin isoalloxine and nicotinamide ring. (Pereira et al., (2001) *Nature Structural Biology* 8, 215-220). Bacterially-expressed and purified recombinant BLVRB$^{WT}$ (wild-type) and BKVRB$^{S111L}$ demonstrated disparate NAD(P)H-dependent redox coupling using both flavin and verdin-specific substrates (FIG. 3b-d). BLVRB$^{S111L}$ enzymatic activity was found to be defective using both flavin mononucleotide (flavin reductase (FR) activity; p<0.0001) and BV IXβ dimethyl esters (biliverdin reductase (BVR) activity; p<0.0001), the latter specifically generated by coupled heme oxidation as verdin-restricted BLVRB activity probes (FIG. 8) (Franklin E M, et al. (2009) *The FEBS journal* 276(16):4405-4413). Additional experiments showed that BLVRB$^{S111L}$ was only 5% as active as BLVRB$^{WT}$ in both the FR (FIG. 3j upper panel) and BVR (FIG. 3j lower panel) assays, indicating that this mutation plays a role in defective redox coupling.

Thus, the S$^{111}$L substitution represents a profound loss-of-function redox mutation with either substrate. Additional expression studies in BLVRB-null human embryonic kidney HEK293 cells confirmed negligible BLVRB$^{S111L}$ BVR activity, with evidence for diminished protein expression, presumably resulting from associated protein misfolding and/or instability (FIG. 3e-f). Nonetheless, BLVRB$^{S111L}$ was readily detectable by immunofluorescent staining (~33% of BLVRB$^{WT}$ as determined by integrated fluorescent intensity), maintaining a conserved (but attenuated) cytoplasmic staining pattern identical to BLVRB$^{WT}$. (FIG. 3g).

The importance of the BV/BR redox cycle in neutralization of reactive oxygen species (ROS) (Nangalia J, et al. (2013) *The New England journal of medicine* 369(25):2391-2405; Klampfl T, et al. (2013) *The New England journal of medicine* 369(25):2379-2390; Niviere V et al., (1996) *The Journal of biological chemistry* 271(28):16656-16661), suggested that defective BLVRB$^{S111L}$ redox coupling could affect ROS accumulation, a requisite upstream signaling messenger of MK differentiation (Motohashi H, et al. (2010) *Blood* 115(3):677-686; Sardina J L, et al. (2010) *Cell death and differentiation* 17(12):1842-1854) and stem cell quiescence during migration from hypoxic (low ROS) osteoblastic to oxygen-rich (high ROS) vascular niches (Owusu-Ansah E & Banerjee U (2009) *Nature* 461(7263):537-541; Suda T, et al., (2011) *Cell stem cell* 9(4):298-310). Hematopoietic-derived (CD34+) induced pluripotent stein cells (iPSC) expressing endogenous BLVRB were initially developed as heterozygous models designed to phenocopy zygosity state in subject cohorts. Lentivirus (Lv/BLVRB$^{WT}$ and Lv/BLVRB$^{S111L}$) infection of iPSCs established that iPSC/BLVRB$^{WT}$ cells (expressing BLVRB 2-fold greater than control) retained enhanced redox activity (p=0.001) compared to both control and iPSC/BLVRB$^{S111L}$ cells. Redox coupling in iPSC/BLVRB$^{S111L}$ paralleled that of control iPSCs (FIG. 3h). Enhanced iPSC/BLVRB$^{WT}$-associated redox coupling was associated with statistically lower baseline ROS accumulation, while baseline ROS accumulation was highest in iPSC/BLVRB$^{S111L}$ cells (FIG. 3i). Incubation with the organic peroxide tert-butyl hydroperoxide (TBHP) as the oxidant stress source protected against ROS accumulation in iPSC/BLVRB$^{WT}$ cells when a TBHP concentration causing ROS accumulation in 50% of either control or iPSC/BLVRB$^{S111L}$ cells (EC$_{50}$ 200 µM) was used. The ROS-neutralizing characteristics of iPSC/BLVRB cells contrasted sharply to those of iPSC/BLVRB$^{S111L}$, which demonstrated exaggerated. TBHP-induced ROS accumulation when compared to either iPSC/BLVRB (p<0.00001) or control iPSCs (p<0.0002).

Exaggerated BLVRB$^{S111L}$ ROS accumulation in the background of endogenous BLVRB expression is paradoxical given the loss-of-function redox mutation, but may be explained by a dominant inhibitory effect during a progressively amplified redox cycle involving dysfunctional BLVRB$^{S111L}$ coupling (Baranano D E, et al., (2002) *Proceedings of the National Academy of Sciences of the United States of America* 99(25):16093-16098). These observations also predict that low-level BLVRB 462$^{C \rightarrow T}$ allelic expression would have exaggerated cellular effects in the background of wild-type C alleles.

Figure 4:
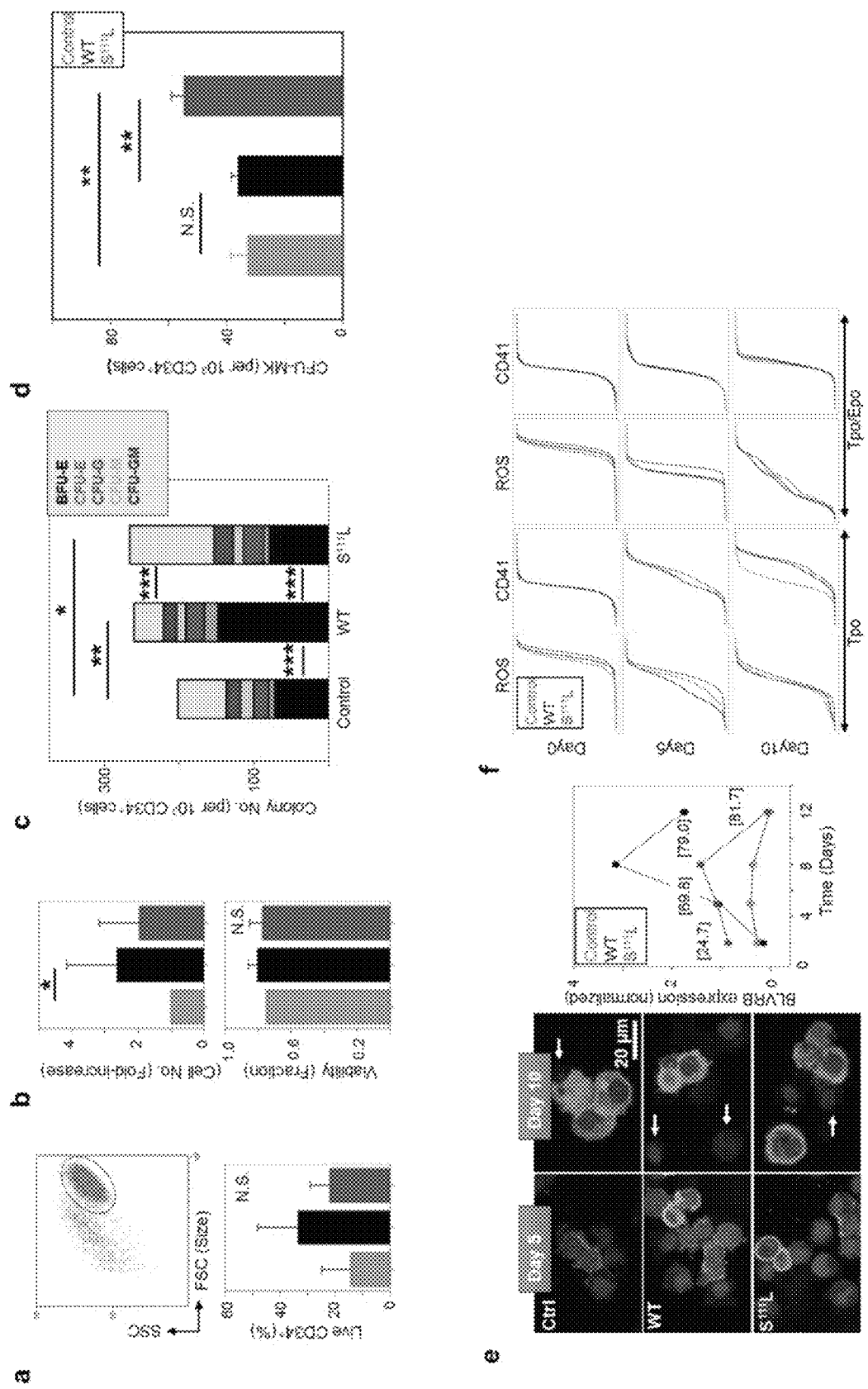
FIG. 4a is a graph showing quantification of CD34$^+$ HSCs transduced with Lv/BLVRB$^{WT}$ (black), Lv/BLVRB$^{S111L}$ (red) or Lv/Control (green). Transduced cells were puromycin-selected and expanded for 48 hours prior to terminal differentiation (Day 0), followed by flow cytometric quantification of gated, live (7-amino-actinomycin D [7-AAD]-negative) CD34+ cells (lower panel, N=4). The upper panel shows flow cytometry gate based on forward (FSC, size) and side (SSC, complexity) scatter of the cells selected for the quantification; *p<0.05; N.S. not significant.
FIG. 4b is a graph showing quantification of CD3++ HSCs (N=6), transduced with Lv/BLVRB$^{WT}$ (black), Lv/BLVRB$^{S111L}$ (red), or Lv/Control (green), prepared as described in FIG. 4a, but expressed as relative fold-increase to control (upper panel) and viability (N=4; lower panel) using trypan blue exclusion. All results are expressed as mean±SEM.
FIG. 4c is a bar graph showing colony/blast forming capacity of genetically-modified CD34+ HSCs. The cells were puromycin-selected and plated for determination of lineage fate using multipotential progenitor assays (N=4 experiments). For each bar in the graph, the compartments from top to bottom correspond to CFU-GEMM, CFU-GM, CFU-GM, CFU-M, CFU-G, CFU-E, and BFU-E, respectively. *p<0.05,  p<0.01; *p<0.001. From left to right, the bars correspond to empty vector control.
FIG. 4d is a bar graph showing CFU-MK determinations (N=9 wells/3 experiments) of genetically-modified CD34+ HSCs that were puromycin-selected and plated for determination of lineage fate using multipotential progenitor assays. *p<0.05, p<0.01; *p<0.001. From left to right the bars correspond to cells derived from empty vector control, BLVRB$^{WT}$ and BLVRB$^{S111L}$ transduced HSCs.
FIG. 4e is a set of immunofluorescence micrographs of genetically-modified CD34+ HSCs differentiated along MK lineage and analyzed by immunofluorescent confocal microscopy for detection of BLVRB (faint outline staining, e.g., see cells pointed to by arrows in middle panel in right column) or CD41 (bright outline staining, e.g., the three cell cluster in top panel in right column) at distinct time points. Arrows demonstrate relative loss of BLVRB in MK/BLVRB$^{S111L}$ and MK/Control compared to that in MK/BLVRB$^{WT}$; size bar is shown. The inset shows a time course of relative BLVRB expression (normalized to actin) as determined by immunoblot, while the numbers in brackets refer to mutant [T] allelic quantification (%) as determined by pyrosequencing analysis; T allele in MK/BLVRB$^{WT}$ and MK/control<3% [assay sensitivity]). The plots from top to bottom correspond to the wild type, mutant (S$^{111}$L, and control respectively.
FIG. 4f is a set of distribution plots for MK phenotypic markers (ROS and CD41), displayed by time point and culture conditions (Tpo or bilineage Tpo/Epo) for cells encompassed within ROS subsets.
FIG. 4g is a graph showing UV-visible spectroscopy of late-stage bilineage cultures (in which CD41−/GlyA+ erythroid fraction accounts for >95% of cells), with no evidence for methemoglobin accumulation in BLVRB$^{S111L}$ erythroid cells.
FIG. 4h is a set of heat maps showing genotype (W-CD34+/BLVRB$^{WT}$; E-CD34+/Control; M-CD34+/BLVRB$^{S111L}$)-restricted differences of key differentiation parameters (ROS—reactive oxygen species, FCS—forward side scatter (size); CD41-Mk) obtained by flow cytometry from megakaryocyte (Tpo) or bilineage (Tpo/Epo) hematopoietic cultures depicted by the day from the start of culturing at which the cytometry was performed. p-values for pairwise comparisons were calculated based on Kolmogorov-Smirnov tests averaged over 200 bootstrapped samples, and are displayed on −log$_{10}$ scale. All results are from a single representative experiment repeated twice.
FIG. 4i is a set of FACS profiles showing ROS accumulation in megakaryocytes derived from cells expressing Lv/control, Lv/BLVRB$^{WT}$, or Lv/BLVRB$^{S111L}$.
Figure 4:
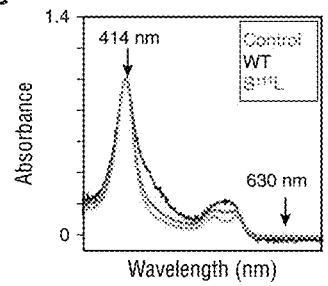
Figure 4:
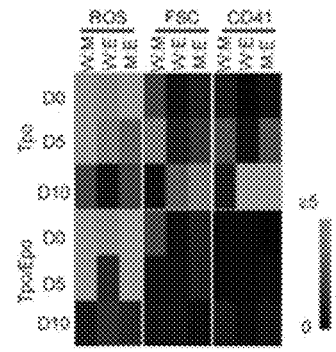
Figure 4:
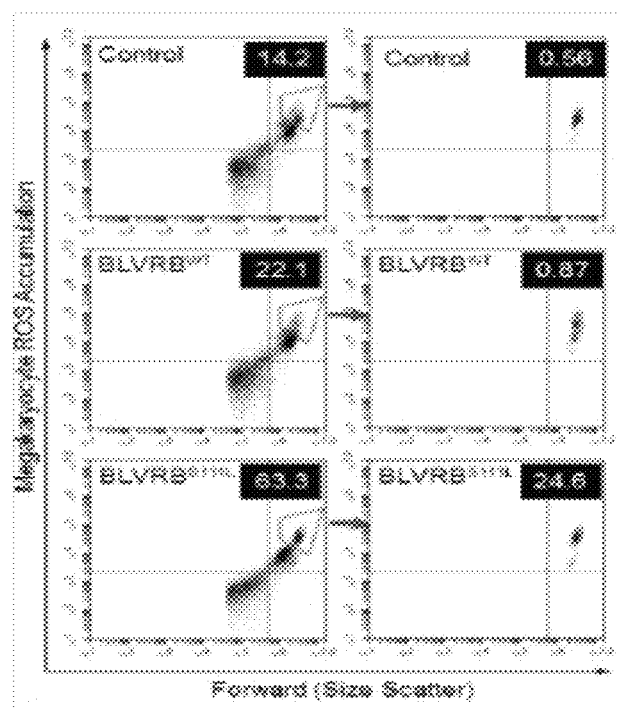

Primary CD34+ hematopoietic stem cells (HSC) transduced with individual lentiviruses demonstrated general expansion of CD34+/BLVRB$^{WT}$ and CD34+/BLVRB$^{S111L}$ progenitor cells compared to CD34+/Control prior to terminal differentiation (Day 0), both by flow cytometry and by cell number, consistent with a proliferative function as previously described for BLVRA (Kapitulnik J & Maines M D (2009) *Trends in pharmacological sciences* 30(3):129-137) (FIG. 4a, b). Excluding ROS-damaging effects resulting from BLVRB$^{S111L}$ expression during initial HSC expansion, there were no differences across the genotypes on cellular viability. Comparative effects of BLVRB-associated redox coupling/ROS handling on lineage commitment using primary CD34+ methylcellulose multipotential progenitor (MPP) cultures confirmed exaggerated aggregate colony formation in Lv/BLVRB$^{WT}$- and Lv/BLVRB$^{S111L}$-transduced cells compared to Lv/Control (FIG. 4c). Conversely, there was disproportionate expansion of primitive CFU-GEMMs (colony forming units, granulocytes/erythrocytes/monocytes/megakaryocytes) CD34+/BLVRB$^{S111L}$ cells (p=0.001), and an absolute increase of BFU-E (burst forming units, erythroid) colonies in CD34+/BLVRB$^{WT}$ cells (p=0.001). Collagen-based cultures designed to specifically quantify MK progenitor potential at a single-cell level demonstrated a statistically-significant increase of CD41+ CFU-MKs in CD34+/BLVRB$^{S111L}$ cells (p<0.01) with no increased CFU-MKs in CD34+/BLVRB$^{WT}$ cells (FIG. 4d), confirming disparate effects on MK lineage commitment and a preserved proliferative function distinct from its redox capacity.

Figure 8:
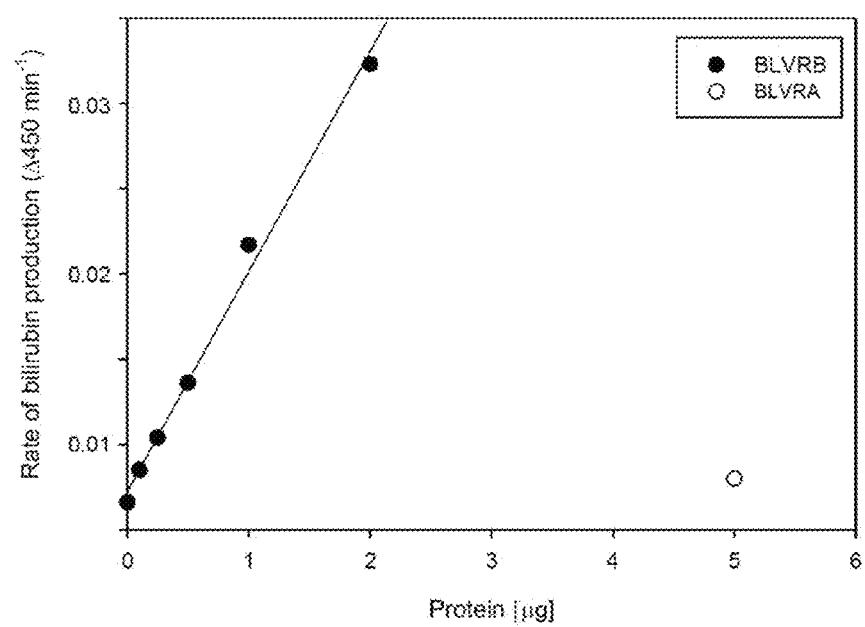
FIG. 8 is a graph for BLVRB enzymatic specificity assay performed using BY IXβ dimethyl esters. BV IXβ dimethyl esters isolated by heme oxidation were assayed for BR generation using varying amounts of recombinant BLVRB or BLVRA. Notably, BLVRA (as high as 5 micrograms) retains no activity for BV IXβ dimethyl esters.

BLVRB functional activity remained below assay threshold sensitivity for all samples throughout the 10-day Tpo-differentiation culture (Cunningham O, et al., (2000) *The Biochemical journal* 345 Pt 2:393-399), although ROS accumulation as a surrogate marker of BLVRB activity remained distinct among the genotypes. CD41-acquisition during terminal differentiation occurs almost exclusively within ROS$^{high}$ cells (Motohashi H, et al. (2010) *Blood* 115(3):677-686; Sardina J L, et al. (2010) *Cell death and differentiation* 17(12):1842-1854) (FIG. 8). Daily cumulative distribution plots of key Mk differentiation parameters (size, CD41+ and ROS intensity) within ROS$^{high}$ subsets confirmed divergent ROS accumulation between MK/BLVRB$^{WT}$ and MK/BLVRB$^{S111L}$ (FIG. 4e-f). ROS-neutralizing effects of MK/BLVRB$^{147}$ sharply contrasted with exaggerated ROS accumulation of MK/BLVRB$^{S111L}$, differences that were identifiable pre-terminal differentiation (Day 0, p=6.5×10$^{-4}$), most pronounced at Day 5 corresponding to peak MK BLVRB expression across genotypes (p=7.7×10$^{-7}$), and persistent at terminal differentiation (Day 10; p=0.05). Across the genotypes and time points, maximally disparate ROS accumulation between CD34+/BLVRB and CD34+/BLVRB$^{S111L}$ at Day 5 corresponded to greatest size disparity and temporally-earlier (and sustained at Day 10) CD41 expression in MK/BLVRB$^{S111L}$ (p=0.03). Presence of >70% mutant T alleles in MK/BLVRB$^{S111L}$ beyond Day 3 confirmed that the mutant T allele was both sufficient and necessary in promoting dysregulated ROS accumulation, which was evident at physiologically modest (~2-fold) increases in BLVRB expression. These results were compared to a bilineage (Tpo/Epo) differentiation model, designed to characterize erythroid/megakarocyte (E/Meg) progenitor balance arising from common MEPs (Debili N, et al. (1996) *Blood* 88(4):1284-1296; Lu J, et al. (2008) *Dev Cell* 14(6):843-853.). Similar to the results in MK cultures, divergent ROS accumulation between BLVRB$^{WT}$ and BLVRB$^{S111L}$ was observed, which was most pronounced at Day 5 of terminal differentiation (p<10$^{-10}$) (FIG. 4f). These differences became more complex at Day 10, likely related to developmentally-heterogeneous stages of maturing erythrocytes exhibiting distinct antioxidant properties (Chen K, et al. (2009) *Proceedings of the National Academy of Sciences of the United States of America* 106(41):17413-17418) [erythrocytes account for >95% of cells in late-stage bilineage cultures (Lu J, et al. (2008) *Dev Cell* 14(6):843-853.)] LTV-visible spectroscopy of day 10 bilineage cultures (normalized to the peak Soret absorbance of oxyhemoglobin [$\lambda_{414}$]) demonstrates no differences in methemoglobin ($\lambda_{630}$) accumulation across the genotypes. (FIG. 4f, 4g, 4h.). Thus, in accordance with the present disclosure BLVRB overexpression increases red blood cell production with no toxicity. Additional experiments were performed which also showed that MKs derived from cells expressing Lv/BLVRB$^{S111L}$ show a marked increase in ROS accumulation when compared to BLVRB$^{WT}$ and control cells (FIG. 4i). Throughout the culture conditions, no evidence for differential (CD41+/Glycophorin A-) lineage balance was observed, suggesting that BLVRB$^{S111L}$ ROS-promoting effects accelerate post-commitment expansion downstream of MEP lineage fate decisions (Debili N, et al. (1996) *Blood* 88(4):1284-1296).

As described above, S$^{111}$L substitution represents a profound loss-of-function mutation with respect to both flavin mononucleotide (flavin reductase (FR) and BV IXβ dimethyl esters (biliverdin reductase (BVR) activity. Also as described above, this loss-of-function mutation is associated with disorders of enhanced platelet production. Accordingly, in one embodiment, the present disclosure provides a method of treating a human or an animal having a disease or disorder that would benefit from increasing platelet counts through inhibition of BLVRB enzymatic activity. The method includes administering to the subject a therapeutically effective amount of an agent that inhibits BLVRB enzymatic activity, thereby treating the subject. Animals contemplated by the present invention include domestic animals such as dogs, cats and rabbits, horses, pigs and livestock. In some embodiments, a "subject" to be treated in accordance with the present disclosure, includes a human or non-human animal.

As used herein "BLVRB enzymatic activity" refers to the activity of BLVRB for reducing biliverdin IXβ to bilirubin IX. The enzymatic activity can be measured using flavin or flavin derivatives (e.g., flavin mononucleotide) as a substrate, in which case the activity is referred to as flavin reductase activity. The enzymatic activity can also be measured using biliverdin or its derivatives (e.g. biliverdin dimethyl esters) s substrate, in which case the activity is referred to as biliverdin reductase activity.

Figure 10:
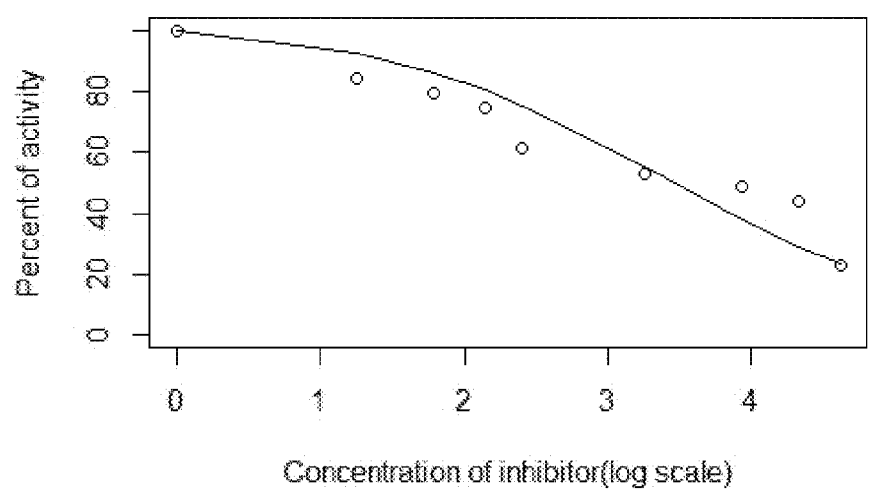
FIG. 10 is a graph for the dose-response of flavin reductase activity of BLVRB as a function of the concentration of compound 1301 shown in Example 9. All data points result from measurements in triplicate.

In one embodiment, the agent is a. chemical compound. An example of such a compound is described in Example 7. Inhibition of enzyme activity by the compound was tested in a reaction containing 100 mM potassium phosphate, pH 7.6, 200 μM FMN (flavin mononucleotide), 100 μM NADPH. The result of inhibition is shown in FIG. 10.

In one embodiment, the BLVRB enzymatic activity is inhibited by at least about 30% to about 100%. For example, the enzyme activity is reduced by about 30% to about 35%, about 35% to about 40%, about 40% to about 45%, about 45% to about 50%, about 50% to about 55%, about 55% to about 60%, about 60% to about 65%, about 65% to about 70%, about 70% to about 75%, about 75% to about 80%, about 80% to about 85%, about 85% to about 90%, about 90% to about 95%, or about 95% to about 100%.

In addition to using an inhibitor to reduce enzymatic activity, one may achieve reduction of the activity also by reducing the expression of the enzyme. Accordingly, in one embodiment, the present disclosure provides a method of treating a human having a disease or disorder that would benefit from increasing platelet counts, such that the expression levels of the enzyme is reduced. The method includes administering to the subject a therapeutically effective amount of an agent that inhibits the expression of biliverdin IXβ reductase (BLVRB) gene, thereby treating the subject. In one embodiment, the agent is a small interfering RNA (siRNA) molecule specific to a region in the mRNA of BLVRB gene. In a related embodiment, the agent is an antisense oligonucleotide specific to a region in the mRNA of BLVRB gene. Methods for reducing expression levels of proteins using either siRNA or antisense oligonucleotides are well-known in the art. For example, see U.S. Pat. Nos. 7,608,707 and 7,674,896 for siRNA, mediated inhibition, and U.S. Pat. Nos. 6,165,990 and 9,078,911 for examples of antisense oligonucleotides mediated inhibition.

In one embodiment, the BLVRB expression is inhibited by at least about 30% to about 100%. For example, the protein expression is reduced by about 30% to about 35%, about 35% to about 40%, about 40% to about 45%, about 45% to about 50%, about 50% to about 55%, about 55% to about 60%, about 60% to about 65%, about 65% to about 70%, about 70% to about 75%, about 75% to about 80%, about 80% to about 85%, about 85% to about 90%, about 90% to about 95%, or about 95% to about 100%.

The present disclosure also envisions a pharmaceutical composition comprising a chemical compound that inhibits the enzymatic activity of BLVRB. Accordingly, in one embodiment, the disclosure provides a pharmaceutical composition comprising a chemical compound that inhibits the enzymatic activity of BLVRB. In one embodiment the pharmaceutical compound reduces the BLVRB enzymatic activity by at least about 30% to about 100%. For example, the enzyme activity is reduced by about 30% to about 35%, about 35% to about 40%, about 40% to about 45%, about 45% to about 50%, about 50% to about 55%, about 55% to about 60%, about 60% to about 65%, about 65% to about 70%, about 70% to about 75%, about 75% to about 80%, about 80% to about 85%, about 85% to about 90%, about 90% to about 95%, or about 95% to about 100%.

According to yet another aspect, the present disclosure provides a pharmaceutical composition that inhibits the expression of BLVRB gene, the composition including a small interfering RNA (siRNA) molecule or an antisense oligonucleotide specific to a region in the mRNA of the gene for BLVRB. In one embodiment, the BLVRB gene expression is inhibited by the pharmaceutical composition comprising the small interfering RNA (siRNA) molecule or the antisense oligonucleotide at least about 30% to about 100%. For example, the enzyme gene expression is reduced by about 30% to about 35%, about 35% to about 40%, about 40% to about 45%, about 45% to about 50%, about 50% to about 55%, about 55% to about 60%, about 60% to about 65%, about 65% to about 70%, about 70% to about 75%, about 75% to about 80%, about 80% to about 85%, about 85% to about 90%, about 90% to about 95%, or about 95% to about 100%.

In one embodiment, the agent is administered at a dose of about 0.01 mg/kg to about 50 mg/kg. In another embodiment, the agent is administered at a dose of about 0.1 mg/kg to about 10 mg/kg.

In one embodiment, the inhibition of BLVRB enzyme activity or BLVRB gene expression leads to increased thrombopoiesis. In one embodiment, the inhibition of BLVRB enzyme activity or BLVRB gene expression leads to accumulation of reactive oxygen species (ROS).

A number of disease or disorder can lead to reduced platelet count. These include decreased production of platelets, increased breakdown of platelets, increased use of platelets, and trapping of platelets in the spleen. In one embodiment, the disease or disorder is one selected from the group comprising: decreased production of platelets, increased breakdown of platelets, increased use of platelets, and trapping of platelets in the spleen. The decreased production of platelets is caused, for example, by one of: cancer, anemia, viral infection, chemotherapy, or heavy alcohol consumption. For example, the cancer is leukemia. Increased breakdown of platelets may be due to pregnancy (usually mild); autoimmune diseases, e.g., lupus and rheumatoid arthritis, in which the immune system attacks and destroys platelets; bacterial infections; and medications, e.g., heparin, quinine, sulfa-containing antibiotics and anticonvulsants, which have the side effect of causing the immune system to destroy platelets. An example of disorder in which there is increased use of platelets is thrombotic thrombocytopenic purpura, which occurs when small blood clots suddenly form throughout the body, using up large numbers of platelets.

TABLE 1

Oligonucleotide primers (5' to 3' orientation)
Q-PCR primer

| Gene | Forward Primer | Reverse Primer |
| --- | --- | --- |
| BLVRA | CTCCCTCTTTGGGGAGCTT | ATTTGGCACATTCTCCAAGG |
| BLVRB | TCCAGGCTGCCATCAGAG | GTCCACACCATGAGCCTTC |
| HMOX1 | GTCAGAGGCCCTGAAGGAG | GAAGTAGACAGGGGCGAAGA |
| HMOX2 | GAAGGAAGGGACCAAGGAAG | CAGCTCCATGGGGAAGTACA |
| PF4 | GAAGACCACCTCCCAGGTC | TGCACACACGTAGGCAGCTA |
| c-MPL | GATACGTGTGCCAGTTTCCA | CTCCTCCCAGCTGATCTGAA |

BLVRB Pyrosequencing Primers
BLVRB gene

| Forward Primer | Reverse Primer | Sequencing Primer |
| --- | --- | --- |
| 5'-ATTGTGGCAGCCATGAAGG-3' | 5'-Biotin-TCAGTCACAGCCTGCAGTCG-3' | 5'-TCGTGGCCTGCACCT-3' |

BLVRB mRNA

| | Reverse Primer | Sequencing Primer |
| --- | --- | --- |
| 5'-ATTGTGGCAGCCATGAAGG-3' | 5'-Biotin-GCTTCAGCGTCACC1TTCAG-3' | 5'-TCGTGGCCTGCACCT-3' |

The present invention is further described by the following non-limiting examples:

EXAMPLES

Example 1: Human Subjects and Data Analyses

All subjects (myeloproliferative neoplasms (MPN), N=36": Reactive Thrombocytosis (RT), N=53: or healthy controls, N=2081 were enrolled in an IRB (Institutional Review Board)-approved protocol conducted in accordance with the Declaration of Helsinki (Gnatenko D V, et al. (2010), Blood 115(1):7-14). Informed consent was obtained from all subjects. Large-scale platelet RNA transcriptomic studies and SNV identification were completed using the Illumina HiSeq 2000 platform (100 ng RNA/sample). Leukocytes isolated by density-gradient centrifugation from sodium citrate-treated blood (0.4% v/v final concentration) served as the source of genomic DNA, while CD45 (leukocyte)-depleted platelet-rich plasma (PRP) served as the source of platelet mRNA. Leukocyte contamination of PRP was $<1\times10^{-5}$, and the isolation, quantification and quality control of both leukocyte and platelet RNAs was established using an Agilent 2100 Bioanalyzer as previously described. (Gnatenko, D. V. et al. (2010) Blood 115, 7-14)

The strategy involved single-end reads and was restricted to nsSNVs to the exclusion of alternative splicing defects and/or insertion/deletions (in/dels). Only nsSNVs identified in at least two ET samples (Tier 1) were used for expanded genotypic studies, which were completed using Illumina human 610 or 660 W SNP arrays (analyzed using GenomeStudio V2010.2 software) or by dideoxy sequence analysis. Five distinct genetic models (genotypic, allelic, trend, dominant and recessive) were applied for the association analyses of each nsSNV [$\chi2$ test, Fisher's exact test, Cochran-Armigage trend test], comparing different case-control groups with genotypic data available from (i) the 1000 Genomes Project Consortium (Anonymous (2012), Nature 491(7422):56-65), (ii) an internal subset of matched healthy controls, or (iii) a cohort subset with reactive thrombocytosis (Gnatenko D V, et al. (2010), Blood 115(1):7-14.). Statistical comparisons were completed using ANOVA or Kolmogorov-Smirnov tests, and all statistical analyses were performed using R version 3.1.2.

Example 2: Platelet RNASeq, Bioinformatic and Genetic Association Analyses

Large-scale platelet RNA transcriptomic studies and SNV identification were completed using the Illumina HiSeq 2000 platform. Briefly, RNA (100 ng/sample) was captured using two rounds of oligo(dT)-coupled beads, followed by cDNA synthesis, library generation, and DNA Sequencing. FASTQ sequence reads truncated as 50 mers were mapped to the human genome Hg19 (February 2009) GRCh37 build with TopHat (Trapnell, C et al., (2009) Bioinformatics 25, 1105-1111), and normalized mRNA abundance for each transcript was calculated using RPKM (reads per kilobase/106) models (Mortazavi, A et al., (2008) Nature methods 5, 621-628). Sequencing coverage ranged from 60- to 100-fold establishing sufficient depth for identification of allelic variation with genotypic frequencies approximating <5%. The strategy involved single-end reads and was restricted to SNVs to the exclusion of alternative splicing defects and/or insertion/deletions (in/dels). For all samples, fragment alignment ranged between 92%-94%. Of the mapped reads, 38% corresponded to mitochondrial genes and 62% to non-mitochondrial genes, consistent with the known prior enrichment of mitochondrial transcripts in platelets. (Gnatenko, D. V. et al., (2003) Blood 101, 2285-2293). SNV calling was performed using SAMtools (htt://samtools.sourceforge.net/). SNV detection stringency conditions included >20% reads calling the variant and quality scores >20. Based on the VCF files, an iterative algorithm to identify MPN-enriched SNVs was developed by applying the following criteria: (i) a minimal SNV quality score of 100 (maximum: 999), (ii) SNVs restricted to non-synonymous mutations which are intrinsically more plausible causative disease candidates (Soler Artigas, M. et al., (2011) *Nature genetics* 43, 1082-1090, doi:10.1038/ng.94), (iii) absence in any of the control samples but present in at least two ET samples (Tier 1 nsSNVs), or present in at 1 ET sample (Tier 2 nsSNVs).

Putative SNVs identified by RNASeq were validated in larger cohorts using Illumina human 610 or 660 W SNP arrays (analyzed using GenomeStudio V2010.2 software) or by dideoxy sequence analysis using leukocyte genomic DNA (20 ng/sample) as template. All SNVs satisfied predicted Hardy-Weinberg equilibrium (HWE) ratios, and five distinct genetic models (genotypic, allelic, trend, dominant and recessive) were applied for the association analyses of each SNV [$\chi 2$ test, Fisher's exact test, Cochran-Armigage trend test (Purcell, S. et al., (2007) *Am J Hum Genet* 81, 559-575)], comparing different case-control groups with genotypic data available from (i) the 1000 Genomes Project Consortium (An integrated map of genetic variation from 1,092 human genomes, (2012) *Nature* 491, 56-65, 15 doi: htt://www.nature.com/nature/journal/17491/n 7422/abs/nature11632.html#supplementary16-information), (ii) 208-matched healthy controls or (iii) a cohort subset with reactive thrombocytosis (RT) (Gnatenko, D. V. et al., (2010) *Blood* 115, 7-14). Odds ratios and confidence intervals were calculated using R version 3.1.2.

Example 3: Quantitative PCR and Pyrosequencing

Cellular RNA quantitation was performed using fluorescence-based real-time PCR (polymerase chain reaction) technology (TaqMan Real-Time PCR; Applied Biosystems, Foster City, Calif.). Oligonucleotide primer pairs were generated using Primer3 software (www-genome.wi.mit.edu), designed to generate approximately 200-base pair (bp) PCR products at the same annealing temperature. The primer sequences are shown in Table 1. Purified platelet mRNA (20 ng) was used for first-strand cDNA synthesis using oligo (dT) and SuperScript II reverse transcriptase (Invitrogen). For real-time reverse transcription (RT)-PCR analysis, the RT reaction was equally divided among primer pairs and used in a 40-cycle PCR reaction for each target gene by using the following cycle: 94° C. for 30 seconds, 55° C. for 30 seconds, 72° C. for 1 minute, and 71° C. for 10 seconds (40 cycles total); mRNA levels were quantified by monitoring real-time fluorometric intensity of SYBR green I, and relative mRNA abundance was determined from triplicate assays performed in parallel for each primer pair using the comparative threshold cycle number ($\Delta$-Ct method) normalized to actin mRNA.

Precise quantification of BLVRB C/T alleles was completed on a PyroMarkMD workstation (Biotage, Sweden), and pyrosequencing assays were designed using PyroMark Assay Design software (version 2.0.1.15). RNA (20 ng/sample) was converted to cDNA using reverse transcription (Invitrogen), and PCR-amplified for 40 cycles (94° C.-45 sec, 60° C.-45 sec, 72° C. 20 sec) using forward primer-5'-ATTGTGGCAGCCATGAAGG-3', reverse primer-5'-Biotin-TCAGTCACAGCCTGCAGTCG-3'; sequencing primer: 5'-TCGTGGCCTGCACCT-3'. Dispensation order was as follows: E-S-A-C-T-C-G-T-G-T-G. The ratio of C (wild-type) to T (mutant) allele(s) was calculated using PyroMark MD software (v. 1.0) based on height of internal control peaks and expressed as % of C to T; sensitivity of mutant allele detection was ~3%.

Example 4: Hematopoietic, Cellular, and Biochemical Assays

Lentiviruses expressing BLVRB (LV/BLVRB), $BLVRB^{S111L}$ (Lv/$BLVRB^{S111L}$) or empty virus control (Lv/Control) driven by the cytomegalovirus promoter and containing the puromycin-resistant cassette were generated at the Stony Brook Stem Cell Viral Vector Core, and used for human CD34$^+$ hematopoietic stem cell assays as previously described (Xu X, et al. (2012) *Blood* 120(17):3575-3585.). Vesicular stomatitis virus-pseudotyped lentiviruses were generated in 293T cells, and concentrated stocks were titered in NIH-3T3 cells. Transduction efficiencies in 293T cells for all viruses were comparable with infectious units titers as follows: Lv/BLVRB (3.1×107/mL), Lv/$BLVRB^{S111L}$ (1.2× 10$^7$/mL), and Lv/Control (5.0×10$^6$ /mL). Induced pluripotent stem cells (iPSC) derived from CD34+ human umbilical cords (NCRM1) were obtained from the NIH Center for Regenerative Medicine and propagated in feeder-free cell culture medium (mTeSR, Stem Cell Technologies). Human CD34$^+$ hematopoietic stem cells (HSCs) were obtained from umbilical cord blood using CD34$^+$-immunoselection, and contained >95% CD34$^+$ cells at the start of individual experiments. CD34$^+$ cells were cultured in SFEM II expansion medium for 24-48 hours followed by lentivirus spin-transduction (1000 g, 2 hours at 25° C.) using multiplicity of infection of 5 in the presence of 4 μg/mL polybrene. Cells washed free of lentivirus/polybrene were selected/expanded in the presence of puromycin (2 μg/mL) for 48 hours after infection prior to terminal differentiation; non-infected controls in the presence of puromycin displayed 0% cell viability by 48 hours.

Multipotential progenitor colony assays were completed in methylcellulose cultures using MethoCult (StemCell Technologies, 114034 Optimum) for quantification of hematopoietic progenitors or MegaCult collagen-based semi-solid media (StemCell Technologies) supplemented with 50 ng/mL thrombopoietm, 10 ng/mL IL-6, and 10 ng/mL IL-3 for CFU-Mk progenitor assays. Hematopoietic progenitors (1×103 cells/plate) were morphologically enumerated at day 14, whereas CFU-Mk colony formation was quantified from cells fixed and stained at day 10. Liquid cultures were maintained in puromycin-selected cells using SFEM 11 expansion medium, and two distinct cytokine cocktails for megakaryocyte-restricted [50 ng/mL thrombopoietin], or bilineage erythroid/megakaryocyte [50 ng/mL thrombopoietin and 2 U; nil: 3 erythropoietin] expansion. (Gnatenko D V, et al. (2003) *Blood* 101(6):2285-2293; Lu J, et al. (2008), *Dev cell* 14(6):843-853; Xu X, et al. (2012), *Blood* 120(17):3575-3585).

Cell differentiation was monitored both by Giemsa stain (for morphology) and by flow cytometry, gating on live 7-actinomycin D (7-AAD)-negative cells for immunophenotypic quantification acid lineage specification. Cell-surface marking was completed by incubating cells on ice for 15 minutes with monoclonal antibodies (MAb) FITC-conjugated anti-CD41a [integrin αxIIb, megakaryocyte] and/or phycoerythrin-conjugated anti-CD235a [glycophorin A, erythroid]); intracellular ROS accumulation was completed by incubating cells with the cell-permeant fluorogenic probe CellROX Green [500 nM, 1 hour at 37° C.] (Life Technologies; Carlsbad, Calif.). All gates were set using isotype-matched IgG (negative) controls, or background fluorescence in the absence of CellROX green for ROS detection.

Flow cytometric quantification was completed by data acquisition of 10,000 gated events using logarithmic gain settings for light scatter and fluorescence detection. Alternatively, cells were pelleted at distinct time points for RNA isolation and/or immunoblot analysis. Cell-surface marking and flow cytometry were performed as described in the references Sedlak T W, et al. (2009), *Proceedings of the National Academy of Sciences of the United States of America* 106(13):5171-5176, and Lu Jr, et al. (2008), *Dev Cell* 14(6):843-853), modified for intracellular ROS accumulation using the cell-permeant fluorogenic probe Cell-ROX Green.

Specific activity determination of $BLVRB^{WT}$ and $BLVRB^{S111L}$ were performed using bacterially-expressed recombinant enzymes at 25° C. and using flavin mononucleotide (FMN) or pooled BV dimethyl esters synthesized by coupled oxidation of heme (Franklin E M, et al., (2009) *The FBS journal* 276(16):4405-4413). RIPA-solubilized cytoplasmic lysates (Baranano D E et al., (2002) *Proceedings of the National Academy of Sciences of the United States of America* 99(25):16093-16098) served as the source for cellular BLVRB functional assays using similar experimental conditions.

Example 5: Protein Analyses

BLVRB enzymatic studies were completed using purified, recombinant enzymes and cellular lysates. BLVRBWT and BLVRBS111L open reading frames were PCR-amplified and directionally-cloned into pGEX-KG expression vector for expression as glutathione-S-transferase (GST) fusion proteins. Recombinant clones were fully sequenced and grown at 37° C. in LB medium containing 100 μg/ml ampicillin and induced with 0.1 mM IPTG for 3 hours. Cells were harvested, lysed by sonication and the supernatant applied to a glutathione sepharose column pre-equilibrated with phosphate-buffered saline. Individual GST-BLVRB fusion proteins were eluted using 10 mM glutathione, excess glutathione was removed by gel filtration (Sephadex G-25), and fusion protein(s) were cleaved overnight at 4° C. with 1 nM thrombin, resulting in >95% separation from the carrier. The cleaved protein was re-passed through a glutathione sepharose column, followed by a final gel filtration step on Sephacryl S-200 for isolation of both reductases which were >85% pure as established by SDS-PAGE and densitography; the presence of S111L mutation was confirmed by tryptic digestion and matrix-assisted laser desorption/ionization (MALDI) mass spectroscopy.

Flavin reductase studies were carried out under saturating concentrations of flavin mononucleotide (FMN, 150 μm) and NAD(P)H (100 μm) in 100 mm potassium phosphate, pH 7.4 at 25° C. Activity was monitored by following the decrease in absorbance of NAD(P)H at 340 nm, and enzymatic activity was calculated using Beer-Lambert's law and a millimolar extinction coefficient of 6.22 $mM^{-1}$ $cm^{-1}$ for NAD(P)H (Yubisui, T et al., (1979) *Journal of biochemistry* 85, 719-728). Biliverdin reductase assay was completed using pooled BV IX isomers generated from coupled heme oxidation as previously described (Bonnett, R. & Dimsdale, M. J., (1972) *Journal of the Chemical Society. Perkin transactions* 1 20, 21 2540-2548) using 25 mg of heme to generate linear free acids (Franklin, E. M. et al., (2009) *The FEBS journal* 276, 4405-24 4413), followed by esterification of the resulting free acids with BF3/MeOH (14% boron trifluoride/methanol) to generate dimethyl esters (BV IXα, BV IXβ, BV IXδ, BV IXγ). Pooled, lyophilized preparations from three 25 mg heme oxidation reactions were dissolved in methanol supplemented with 37 μm BSA to aid solubilization, and four distinct isomers were readily separated and visualized by thin layer chromatography. All assays were conducted at 25° C. in Tris buffer, pH 8.7, containing 100 μm NADPH and pooled BV isomers at a concentration of 20 μm (the final concentration of methanol in the assay mix never exceeded 1% and does not interfere with enzymatic activity (Cunningham, O et al., (2000) *The Biochemical journal* 345 Pt 2, 393-27 399). Spectral quantification (450 nm) of the corresponding bilirubins was completed using a Cary 60 UV/V is spectrophotometer, and the rate of enzymatic activity was calculated using Beer-Lambert's law and a millimolar extinction coefficient of 20.5 $mM^{-1}$ $cm^{-1}$ for bilirubin IXβ (Yamaguchi, T et al., (1994) *The Journal of biological chemistry* 269, 24343-24348); enzymatic activity is expressed as nanomoles of bilirubin $min^{-1}$ $mg^{-1}$ protein.

Cellular lysates using HEK 293 cells infected with lentiviruses were lysed in buffer containing 50 mM HEPES, pH 7.4, 75 mM NaCl, 20 mM $MgCl_2$, 1% Nonidet-P-40, 2 mM EDTA, protease inhibitor cocktail (AEBSF, aprotinin, bestatin, E-64, leupeptin, and pepstain A) and phosphatase inhibitor cocktail (imidazole, sodium fluoride, sodium molybdate, sodium orthovanadate, and sodium tartrate dihydrate). Cells were disrupted by use of a Dounce homogenizer and cellular debris was removed by centrifugation at 10,000×g for 20 minutes at 4° C., followed by biliverdin reductase assays as outlined above.

Immunodetection was completed using gel-filtered platelets solubilized in [50 mM. Tris, 150 mM NaCl, 1% NP40, 0.5% deoxychoate, supplemented with 0.01 v/v proteolytic inhibitor cocktail (Sigma)] while genetically modified cells (HEK293, NCRM1) were specifically solubilized in 1×RIPA buffer (Rockland Immunochemicals) supplemented with the identical proteolytic inhibitors cocktail. Protein immunodetection was completed using 4-15% gradient sodium dodecyl sulfate (SDS)-polyacrylamide gel electrophoresis (PAGE) and immunoblot analysis using the species-specific horseradish peroxidase-conjugated secondary antibody and enhanced chemiluminescence. Primary antibodies included sheep anti-human BLVRB (R&D Systems, Minnesota; 1:100 dilution) and anti-actin MAb (EMD Millipore, U.S.A.; 1:1,000). Relative protein abundance was normalized to actin using densitometric analysis (Gel-Pro Analyzer. Software; Media Cybernetics).

Example 6: Cell-Based Assays and Fluorescence Microscopy

Human $CD34^+$-derived NCRM1 induced pluripotent stem cells (iPSC) were genetically modified using lentivirus infection (MOI 9) for generation of stable cell lines after puromycin selection (iPSC/$BLVRB^{S111L}$, iPSC/$BLVRB^{WT}$, iPSC/Control). Oxidation/reduction activity was quantified in vitro using the NADPH-dependent redox coupler resazurin; cells ($4 \times 10^4$/well) were plated and propagated in mTeSR1 medium and at 24 hours were incubated with resazurin (0.1 v/v) followed by serial spectrofluorimetric detection (530 nm excitation, 590 nm emission) for the reduced resorufin byproduct. Cytoprotective effects were studied by plating genetically-7 modified iPSCs (iPSC/$BLVRB^{S111L}$, iPSC/$BLVRB^{WT}$, iPSC/Control) at cell densities of $5 \times 10^5$/mL, followed by ROS induction (or not) using varying doses of the organic peroxide tert-9 butyl hydroperoxide (TBHP) for 1 hour at 37° C.; subsequently, cells were incubated with cell-permeable 500 nM CellROX Green (Life Technologies, Carlsbad, Calif.) for 60 minutes at 37° C. for fluorescent detection of ROS (485 nm excitation, 520 nm emission) by flow cytometry.

Immunofluorescent microscopy (HEK 293 cells, CD34+-differentiated HSCs) was completed on cytocentrifuged samples that were fixed and permeabilized using 10% formalin/0.25% Triton X, followed by immunodetection using anti-BLVRB (R and D Systems; 1:100 sheep anti-human at 4° C. overnight), anti-CD41 (Stem Cell Technologies; 1:50 mouse anti-human at 4° C. overnight), or anti-glycophorin A (MyBioSource 1:50) using species-specific antibodies Alexi Fluor AF488 donkey anti-mouse (Life Technologies; 1:1600 for 60 minutes at 25° C.) or AF594 anti-sheep CD41 (Life Technologies; 1:1600 for 60 minutes at 25° C.); after final rinse, cells were mounted onto glass coverslips using Prolong Gold antifade/DAPI (4',6-Diamidino-2-Phenylindole, Dilactate) for nuclear visualization. All images were captured under identical exposure times using a Leica SP5 X laser scanning confocal microscope; image processing for comparative fluorescence BLVRB quantification was completed using Cellprofiler (version 2.1.1), adjusted for background fluorescence of BLVRB-stained mock-infected controls.

Example 7: Inhibition of BLVRB by a Chemical Compound

An in vitro enzymatic assay screen of ten compounds identified from an initial round of in silky screening (using the previously-published BLVRB crystal structure liganded to NADPH cofactor and biliverdin IXα) against the NCI Diversity Set IV database (consisting of 2,000 small molecules subselected from the full NCI screening collection) was carried out which led to the identification of compound 1301 (NSC 130813; structure shown below) as the most potent inhibitor of the flavin reductase activity of biliverdin IX beta reductase (BLVRB).

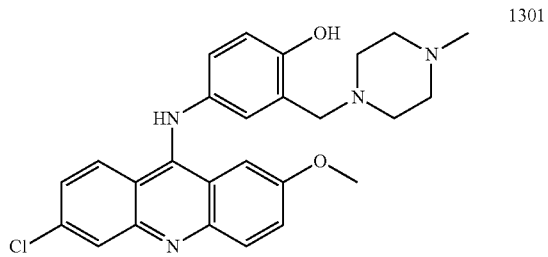 [SMILES: COc1ccc2nc3cc(Cl)ccc3c(Nc3ccc(O)c(CN4CCN(C)CC4)c3)c2c1]

1301

Figure 9:
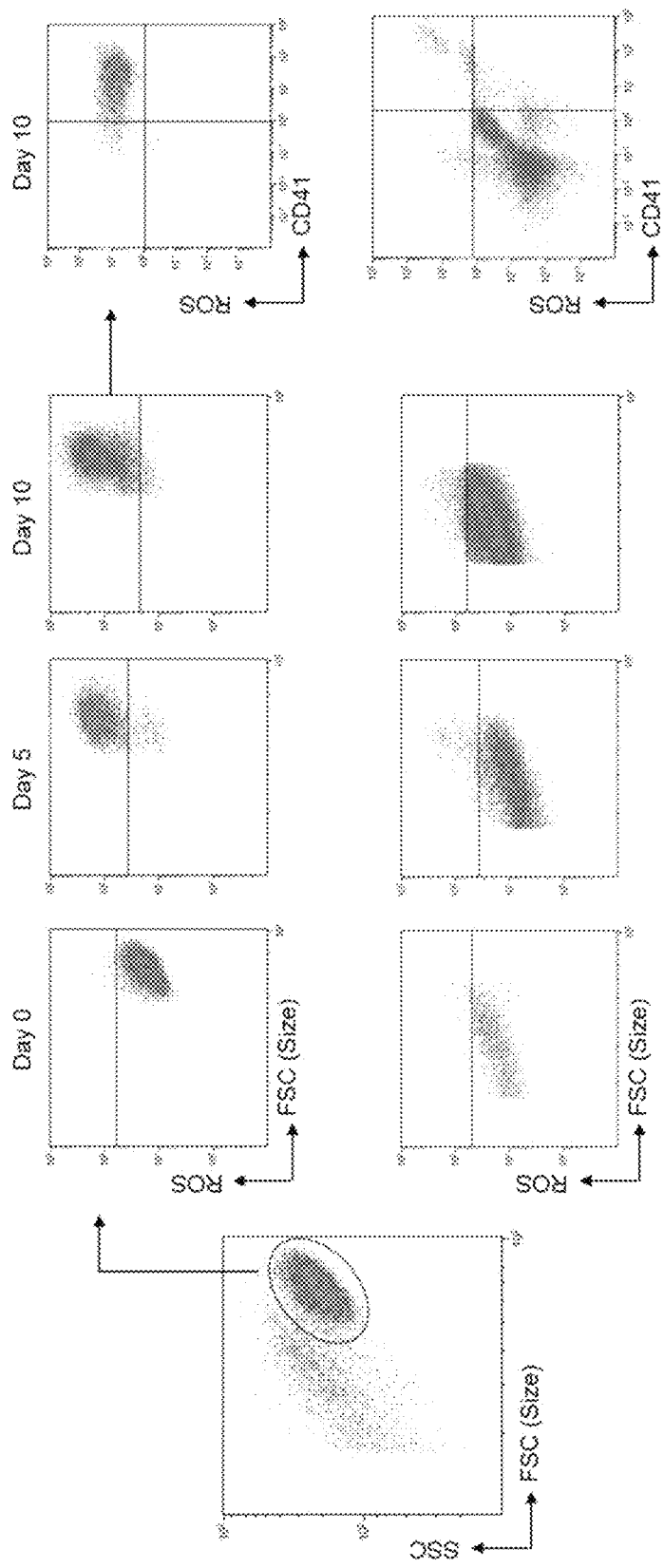
FIG. 9 shows plots for flow cytometry of CD34+ cells. Live (7-AAD-negative) CD34+ cells initially identified by forward (FSC) and side (SSC) scatter (defined gate is depicted on the left) represent the multipotential progenitor population retaining the capacity for ROS$^{high}$ accumulation and CD41-generation upon terminal differentiation in the presence of Tpo (upper rows) compared to non-gated ROS$^{low}$ subsets (lower rows). Notably, the expanded cells at Day 0, prior to Tpo-supplementation, are ROS$^{low}$.

Potential inhibitors of BLVRB were assayed in a reaction containing 100 mM potassium phosphate, pH 7.6, 200 μM FMN (flavin mononucleotide), 100 μM NADPH and various concentrations of inhibitor (based on solubility in the reaction mixture at 37° C.). Reactions were initiated by the addition of 300 nM recombinant BLVRB. Enzymatic activity was monitored by following the decrease in absorbance at 340 nm which corresponds to the oxidation of NADPH to $NADP^+$. The $IC_{50}$, concentration of inhibitor needed to inhibit the target enzyme by 50%, of compound 1301 was determined to be 30.7 μM. (FIG. 9)

Example 8: Biostatistics

Statistical comparisons were completed using ANOVA or Kolmogorov-Smirnov tests, and all statistical analyses were performed using R version 3.1.2. The relative enrichment of candidate gene set was determined using the Wilcoxon-Mann-Whitney test, comparing the rankings of 38-member hematopoietic gene atlas relative to all other genes that were expressed in at least one time point by lineage.

EQUIVALENTS

Those skilled in the art will recognize, or be able to ascertain using no more than routine experimentation, many equivalents to the specific embodiments and methods described herein. Such equivalents are intended to be encompassed by the scope of the following claims.

What is claimed is:

1. A method of increasing platelet counts of a subject, the method comprising:
administering to the subject therapeutically effective amount of an agent that inhibits biliverdin IXβ reductase (BLVRB) enzymatic activity, wherein the agent is 4-((6-Chloro-2-methoxyacridin-9-yl)amino)-2-((4-methylpiperazin-1-yl)methyl)phenol and wherein the agent increases the platelet count of the subject.

2. The method of claim 1, wherein the BLVRB enzymatic activity is inhibited by at least about 30% to about 100%.

3. A method of increasing platelet counts of a subject, the method comprising:
administering to the subject therapeutically effective amount of an agent that inhibits biliverdin IXβ reductase (BLVRB) enzymatic activity and increases the platelet count of the subject.

4. The method of claim 1, wherein the agent is administered at a dose of about 0.01 mg/kg to about 50 mg/kg.

5. The method of claim 1, wherein the inhibition of BLVRB enzymatic activity or BLVRB gene expression leads to increased thrombopoiesis.

6. The method in claim 1, wherein the inhibition of BLVRB enzymatic activity or BLVRB gene expression leads to accumulation of reactive oxygen species (ROS).

7. The method of claim 3, wherein decreased production of platelets is caused by chemotherapy.

8. The method of claim 1 wherein the subject is a human.

9. The method of claim 1 wherein the subject is an animal.

10. The method of claim 3, wherein the agent is administered at a dose of about 100 mg/kg.

11. The method of claim 3, wherein the agent is 4-((6-Chloro-2-methoxyacridin-9-yl)amino)-2-((4-methylpiperazin-1-yl)methyl)phenol.

12. The method of claim 3 wherein the subject is a human.

13. The method of claim 3 wherein the subject is an animal.

* * * * *